US009938364B2

(12) United States Patent
Canich et al.

(10) Patent No.: US 9,938,364 B2
(45) Date of Patent: Apr. 10, 2018

(54) SUBSTITUTED METALLOCENE CATALYSTS

(71) Applicant: ExxonMobil Chemical Patents Inc., Baytown, TX (US)

(72) Inventors: Jo Ann M. Canich, Houston, TX (US); Peijun Jiang, League City, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 15/279,144

(22) Filed: Sep. 28, 2016

(65) Prior Publication Data
US 2017/0015767 A1     Jan. 19, 2017

Related U.S. Application Data

(63) Continuation-in-part of application No. 14/325,449, filed on Jul. 8, 2014, now Pat. No. 9,458,254, and a continuation-in-part of application No. 14/325,474, filed on Jul. 8, 2014, now Pat. No. 9,458,260.

(60) Provisional application No. 61/847,442, filed on Jul. 17, 2013.

(51) Int. Cl.
C08F 4/6592 (2006.01)
C08F 210/02 (2006.01)
C08F 210/16 (2006.01)
C08F 210/18 (2006.01)
C07F 17/00 (2006.01)
C08F 4/659 (2006.01)

(52) U.S. Cl.
CPC ............ C08F 210/02 (2013.01); C07F 17/00 (2013.01); C08F 4/65908 (2013.01); C08F 4/65912 (2013.01); C08F 210/16 (2013.01); C08F 210/18 (2013.01)

(58) Field of Classification Search
CPC .. C08F 4/65927; C08F 210/02; C08F 210/16; C08F 210/18
See application file for complete search history.

(56) References Cited

U.S. PATENT DOCUMENTS

| | | |
|---|---|---|
| 4,814,540 A | 3/1989 | Watanabe et al. |
| 5,049,535 A | 9/1991 | Resconi et al. |
| 5,276,208 A | 1/1994 | Winter et al. |
| 5,278,264 A | 1/1994 | Spaleck et al. |
| 5,304,614 A | 4/1994 | Winter et al. |
| 5,459,117 A | 10/1995 | Ewen |
| 5,532,396 A | 7/1996 | Winter et al. |
| 5,543,373 A | 8/1996 | Winter et al. |
| 5,585,509 A | 12/1996 | Langhauser et al. |
| 5,631,202 A | 5/1997 | Ewen |
| 5,667,408 A | 9/1997 | Broschard et al. |
| 5,696,045 A | 12/1997 | Winter et al. |
| 5,700,886 A | 12/1997 | Winter et al. |
| 5,739,366 A | 4/1998 | Imuta et al. |
| 5,767,033 A | 6/1998 | Imuta et al. |
| 5,770,753 A | 6/1998 | Küber et al. |
| 5,786,432 A | 7/1998 | Küber et al. |
| 5,840,644 A | 11/1998 | Küber et al. |
| 5,869,584 A | 2/1999 | Winter et al. |
| 6,051,727 A | 4/2000 | Küber et al. |
| 6,057,048 A | 5/2000 | Winter et al. |
| 6,057,408 A | 5/2000 | Winter et al. |
| 6,121,182 A | 9/2000 | Okumura et al. |
| 6,136,743 A | 10/2000 | Sugimura et al. |
| 6,150,481 A | 11/2000 | Winter et al. |
| 6,242,544 B1 | 6/2001 | Küber et al. |
| 6,255,506 B1 | 7/2001 | Küber et al. |
| 6,355,819 B1 | 3/2002 | Leino et al. |
| 6,380,331 B1 | 4/2002 | Kuchta et al. |
| 6,399,533 B2 | 6/2002 | Sacchetti et al. |
| 6,444,833 B1 | 9/2002 | Ewen et al. |
| 6,492,465 B1 | 12/2002 | Burkhardt et al. |
| 6,559,252 B1 | 5/2003 | Horton et al. |
| 6,608,224 B2 | 8/2003 | Resconi et al. |
| 6,635,779 B1 | 10/2003 | Ewen et al. |
| 6,787,618 B1 | 9/2004 | Winter et al. |
| 6,841,501 B2 | 1/2005 | Resconi et al. |
| 6,878,786 B2 | 4/2005 | Resconi et al. |
| 6,949,614 B1 | 9/2005 | Schottek et al. |
| 6,953,829 B2 | 10/2005 | Kratzer et al. |
| 7,034,173 B2 | 4/2006 | Schottek |
| 7,122,498 B2 | 10/2006 | Hart et al. |
| 7,141,527 B1 | 11/2006 | Van Baar et al. |
| 7,220,695 B2 | 5/2007 | Casty et al. |
| 7,314,903 B2 | 1/2008 | Resconi et al. |

(Continued)

FOREIGN PATENT DOCUMENTS

| | | |
|---|---|---|
| CN | 101074276 A | 11/2007 |
| EP | 576970 | 1/1994 |

(Continued)

OTHER PUBLICATIONS

U.S. Appl. No. 14/325,474, filed Jul. 8, 2014, Canich et al.
Caldwell et al., "Are Perpendicular Alkene Triplets Just 1,2-Biradicals? Studies with the Cyclopropylcarbinyl Clock", Journal of the American Chemical Society, Mar. 1994, vol. 116, No. 6, pp. 2271-2275.
Deng et al., "Nickel-catalyzed Carboannulation Reaction of o-Bromobenzyl Zinc Bromide with Unsaturated Compounds", Organic Letters, 2007, vol. 9, No. 25, pp. 5207-5210.
de Meijere et al., "An Efficient Three-Step Synthesis of Cyclpenta[b]pyrans via 2-Donor-Substituted Fischer Ethenylcarbenechromium Complexes", Chemistry: A European Journal, 2005, Wiley-VCH Verlag GmbH & Co. KGaA, Weinheim, vol. 11, pp. 4132-4148.
Izmer et al., "Synthesis and Molecular Structures of Zirconium and Hafnium Complexes Bearing Dimethylsilandiyl-bis-2,4,6-trimethylindenyl and Dimethylsilandiyl-bis-2-methyl-4,6-diisopropylindenyl Ligands", Journal of Organometallic Chemistry (2005), vol. 690, Issue 4, pp. 1067-1079.
Kaneyoshi, H. et al., "Synthesis of Block and Graft Copolymers with Linear Polyethylene Segments by Combination of Degenerative Transfer Coordination Polymerization and Atom Transfer Radical Polymerization," Macromolecules, vol. 38, Issue 13, 2005, pp. 5425-5435.

(Continued)

Primary Examiner — Caixia Lu

(57) ABSTRACT

This invention relates to novel bridged a hafnium transition metal metallocene catalyst compounds having two indenyl ligands substituted at the 4 position, preferably 4 and 7 positions, with a $C_1$ to $C_{10}$ alkyl, where the 2 and 3 positions are hydrogen (assuming the bridge position is counted as the one position) and the bridging atom is carbon or silicon which is incorporated into a cyclic group comprising 3, 4, 5, or 6 silicon and/or carbon atoms that make up the cyclic ring.

29 Claims, 1 Drawing Sheet

(56) References Cited

U.S. PATENT DOCUMENTS

| | | | |
|---|---|---|---|
| 7,342,078 B2 | 3/2008 | Schottek et al. |
| 7,385,015 B2 | 6/2008 | Holtcamp |
| 7,405,261 B2 | 7/2008 | Schulte et al. |
| 7,452,949 B2 | 11/2008 | Okumura et al. |
| 7,569,651 B2 | 8/2009 | Schottek et al. |
| 7,615,597 B2 | 11/2009 | Resconi et al. |
| 7,741,417 B2 | 6/2010 | Casty et al. |
| 7,799,880 B2 | 9/2010 | Ciaccia |
| 7,829,495 B2 | 11/2010 | Floyd et al. |
| 7,964,679 B2 | 6/2011 | Resconi et al. |
| 7,985,799 B2 | 7/2011 | Resconi et al. |
| 8,008,653 B2 | 8/2011 | Lee et al. |
| 8,222,356 B2 | 7/2012 | Kipke et al. |
| 2002/0019504 A1 | 2/2002 | Sunaga et al. |
| 2002/0103312 A1 | 8/2002 | Rausch et al. |
| 2003/0120015 A1 | 6/2003 | Resconi et al. |
| 2003/0149199 A1 | 8/2003 | Schottek et al. |
| 2004/0132933 A1 | 7/2004 | Crowther |
| 2004/0132935 A1 | 7/2004 | Arjunan et al. |
| 2005/0182266 A1 | 8/2005 | Schulte et al. |
| 2005/0228155 A1 | 10/2005 | Kawai et al. |
| 2005/0261449 A1 | 11/2005 | Voskoboynikov et al. |
| 2006/0116490 A1 | 6/2006 | Paczkowski et al. |
| 2009/0259007 A1 | 10/2009 | Ciaccia |
| 2009/0318640 A1 | 12/2009 | Brant |
| 2010/0249346 A1 | 9/2010 | Schiendorfer et al. |
| 2010/0261860 A1 | 10/2010 | Schulte et al. |
| 2010/0267907 A1 | 10/2010 | Dimeska et al. |
| 2011/0230630 A1 | 9/2011 | Sell et al. |
| 2012/0095157 A1 | 4/2012 | Jiang et al. |
| 2012/0245299 A1 | 9/2012 | Jiang et al. |
| 2013/0085232 A1 | 4/2013 | Stewart |
| 2013/0150541 A1 | 6/2013 | Crowther et al. |

FOREIGN PATENT DOCUMENTS

| | | |
|---|---|---|
| EP | 0812854 | 12/1997 |
| EP | 812854 | 12/1997 |
| EP | 1209165 | 5/2002 |
| EP | 1520863 | 4/2005 |
| EP | 1520863 | 6/2005 |
| JP | 53-37644 | 4/1978 |
| JP | 55-10599 | 3/1980 |
| JP | 08-0239416 | 9/1996 |
| RU | 2160276 | 12/2000 |
| WO | 97/40075 | 10/1997 |
| WO | 98/46616 | 10/1998 |
| WO | 2000/068279 | 11/2000 |
| WO | 01/48034 | 7/2001 |
| WO | 02/02575 | 1/2002 |
| WO | 02/02576 | 1/2002 |
| WO | 03/002583 | 1/2003 |
| WO | 03/045551 | 6/2003 |
| WO | 03/050131 | 6/2003 |
| WO | 2003/050131 | 6/2003 |
| WO | 04/017602 | 2/2004 |
| WO | 07/070040 | 6/2007 |
| WO | 2007/070040 | 6/2007 |
| WO | 08/027116 | 3/2008 |
| WO | 2010/077230 | 7/2010 |
| WO | 2011/051705 | 5/2011 |
| WO | 2012/134715 | 10/2012 |
| WO | 2015/009479 | 1/2015 |

OTHER PUBLICATIONS

Mochalov et al., "*Transformations of Arylcyclopropanes Under the Action of Dinitrogen Tetroxide*", Journal of Organic Chemistry of the USSR (Translation of Zhurnal Organicheskoi Khimii) (1998), vol. 34, Issue 9, pp. 1322-1330.

Mochalov et al., "*Nitration of Biphenylcyclopropanes*", Journal of Organic Chemistry of the USSR (Zhurnal Organicheskoi Khimii), May 1976, vol. 12, Issue 5, pp. 1008-1014.

Ransom et al., "*Synthesis and Molecular Structures of Zirconium and Hafnium Complexes Bearing Dimethylsilandiyl-bis-2,4,6-trimethylindenyl and Dimethylsilandiyl-bis-2-methyl-4,6-diisopropylindenyl Ligands*", Organometallics (2011), vol. 30, Issue 4, pp. 800-814.

Riemschneider et al., "*Chemistry of Polyhalocyclopentadienes and Related Compounds. XVII. Reaction of Hexachlorocyclopentadiene with Unsaturated Compounds*", Monatshefte fuer Chemie, 1960, vol. 91, Issue 1, pp. 22-40. (English language abstract attached.).

Rulhoff et al., "*Synthesis and Characterization of Propylene and Linear Ethylene Oligomers ($C_n$=26-28) with Metallocenes/MAO Catalysts*," Macromolecular Chemistry and Physics, vol. 207, Issue 16, 2006, pp. 1450-1460.

Shabarov et al., "*Reaction of 2-cyclpropylfluorene with Mercury Acetate*", Vestnik, Moskovskogo Universiteta, Seriya 2: Khimiya, Moscow University Chemistry Bulletin, 1976, vol. 17, Issue 5, pp. 620-621.

Waugh et al., "*Upper Excited State Photochemistry: Solution and Gas Phase Photochemistry and Photophysics of 2- and 3-Cyclopropylindene$^1$*", Journal of the American Chemical Society, Mar. 1999, vol. 121, Issue 13, pp. 3083-3092.

Yoshida, Z., "*Novel Pi Systems Possessing Cyclopropenylidene Moiety*", Pure & Applied Chemistry, vol. 54, No. 5 (1982), pp. 1059-1074.

Resconi et al., "Olefin Polymerization at Bis(pentamethyl-cyclopentadienyl)-zirconium and -hafnium Centers: Chain-Transfer Mechanisms," J. Am. Chem. Soc., Jan. 1992, vol. 114, No. 3, pp. 1025-1032.

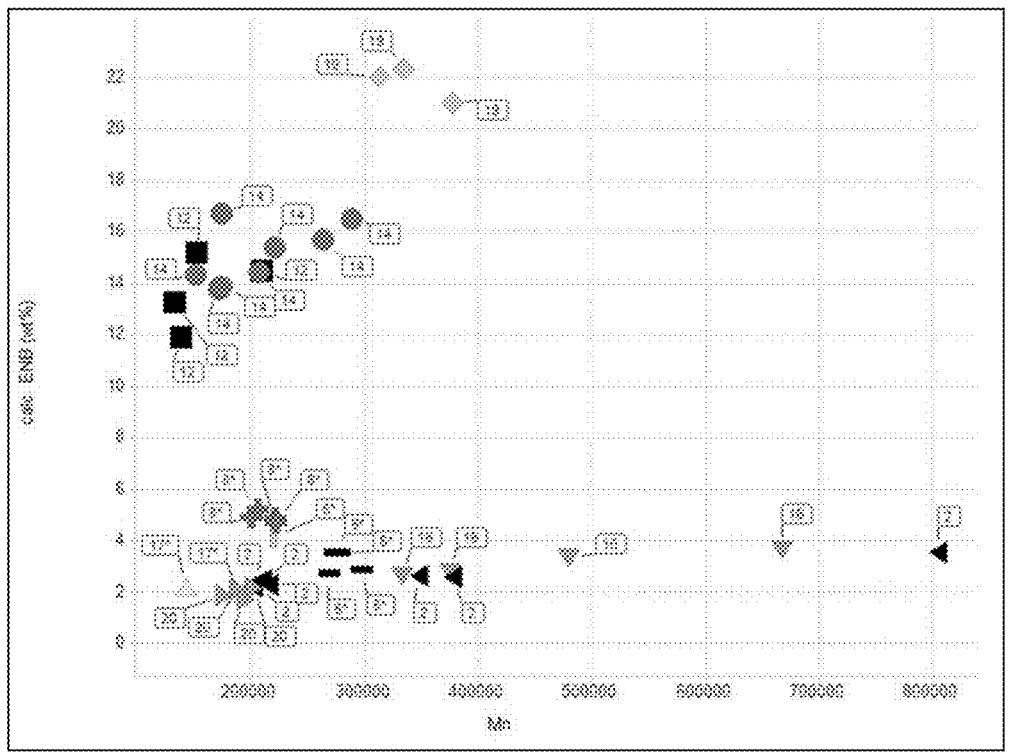

SUBSTITUTED METALLOCENE CATALYSTS

STATEMENT OF RELATED CASES

This application is a continuation in part of U.S. Ser. No. 14/325,449, filed Jul. 8, 2014 which claims the benefit of and priority to U.S. Ser. No. 61/847,442, filed Jul. 17, 2013.

This application is also a continuation in part of U.S. Ser. No. 14/325,474, filed Jul. 8, 2014 which claims the benefit of and priority to U.S. Ser. No. 61/847,442, filed Jul. 17, 2013.

FIELD OF THE INVENTION

This invention relates to novel bridged hafnium metallocene compounds comprising indenyl ligands substituted at the 4 and optionally in the 7 positions.

BACKGROUND OF THE INVENTION

Olefin polymerization catalysts are of great use in industry. Hence there is interest in finding new catalyst systems that increase the commercial usefulness of the catalyst and allow the production of polymers having improved properties.

Catalysts for olefin polymerization are often based on metallocenes as catalyst precursors, which are activated either with the help of an alumoxane, or with an activator containing a non-coordinating anion.

Useful metallocene catalysts have been based upon bis-indenyl transition metal compounds. In particular, bridged bis-2-substituted indenyl transition metal compounds and bridged bis-2,4-disubstituted indenyl transition metal compounds have found use in polymerizing propylene, see for example U.S. Pat. No. 5,276,208 and EP 576 970.

Also see WO 2011/051705 which discloses substituted indenyl compounds, but no cyclic bridging groups. Also see Ransom, et al. Organometallics (2011), 30(4), pp. 800-814 where a series of ansa-bridged ethylene-bis(hexamethylindenyl)zirconium and hafnium complexes were explored. Likewise, see CN 2006-10080838 (also referred to as CN 101074276 B) which appears to use $Me_2Si(2-Me-4-iPrInd)_2 HfCl_2$ to make isotactic polypropylene with branching by adding in functionalized styrene where the functional group is a vinyl group. See also U.S. Pat. No. 7,741,417; U.S. Pat. No. 7,220,695; and WO 2008/027116 where the processes are disclosed to produce isotactic polypropylene by contacting propylene and optionally one or more monomers with a bis-indenyl Group 4 metallocene compound supported on a silica treated with organoaluminum compound(s) and heterocyclic compound(s), under slurry conditions in the presence of hydrogen at a temperature of about 50° C. to about 160° C. and a pressure of from about 3 MPa to about 5 MPa to provide a catalyst activity of greater than 30,000 lb of product per lb of catalyst (note that rac-dimethylsilyl-bis(2-methyl-4,6-diisopropyl-indenyl)hafnium (or zirconium) dimethyl (or dichloride) are listed in the text).

Also see U.S. Pat. No. 7,385,015 where certain bis-indenyl compounds are supported on a support that has been combined with a first trialkylaluminum, calcined, then combined with a second trialkylaluminum compound(s), where the alkyl groups have two or more carbon atoms and the first and second trialkylaluminum compound(s) may be the same or different. Note that rac-dimethylsilyl-bis(2-methyl-4,6-diisopropyl-indenyl)hafnium (or zirconium) dimethyl (or dichloride) are listed in the text as catalysts that can be supported and dimethylsilylbis(2-methyl-4-phenyl)hafnium dimethyl is used in the examples.

U.S. Pat. No. 7,220,695 and U.S. Pat. No. 7,741,417 disclose supported activators of an ion-exchanged layered silicate, an organoaluminum compound, and a heterocyclic compound, which may be substituted or unsubstituted. Note that rac-dimethylsilyl-bis(2-methyl-4,6-diisopropyl-indenyl)hafnium (or zirconium) dimethyl (or dichloride) are listed in the text as catalysts that can be supported and dimethylsilylbis(2-methyl-4-phenyl)hafnium dimethyl is used in the examples.

See also "Synthesis and molecular structures of zirconium and hafnium complexes bearing dimethylsilandiyl-bis-2,4, 6-trimethylindenyl and dimethylsilandiyl-bis-2-methyl-4,6-diisopropylindenyl ligands" Izmer et al., Journal of Organometallic Chemistry (2005), 690(4), pp. 1067-1079 which describes zirconium and hafnium ansa-complexes containing 2,4,6-trialkyl-substituted indenyl fragments, such as rac- and meso-$Me_2Si(2-Me-4,6-R_2C_9H_3-\eta^5)_2MCl_2$ (R=Me, iPr; M=Zr, Hf) The complexes reproduced below were disclosed. No polymerizations using these compounds were performed.

Scheme 6.

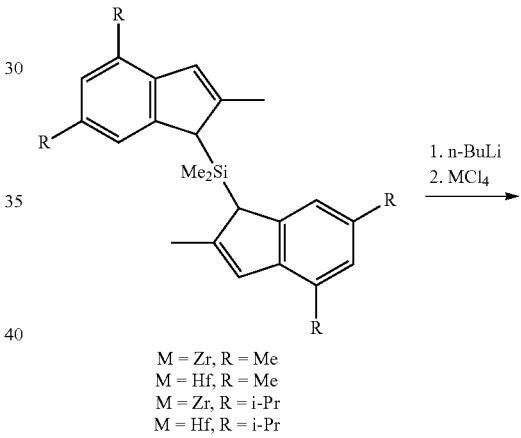

M = Zr, R = Me
M = Hf, R = Me
M = Zr, R = i-Pr
M = Hf, R = i-Pr

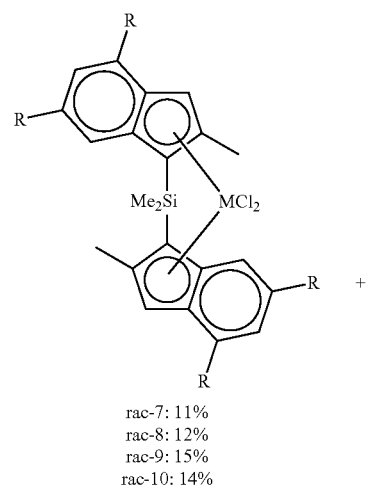

rac-7: 11%
rac-8: 12%
rac-9: 15%
rac-10: 14%

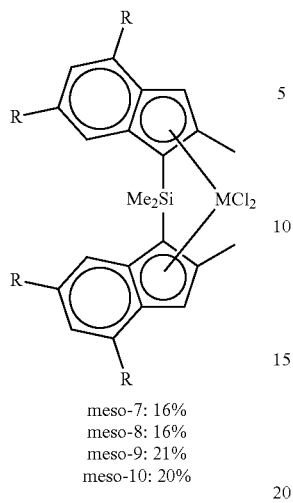

meso-7: 16%
meso-8: 16%
meso-9: 21%
meso-10: 20%

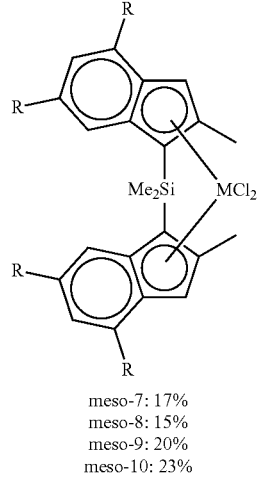

meso-7: 17%
meso-8: 15%
meso-9: 20%
meso-10: 23%

Scheme 7.

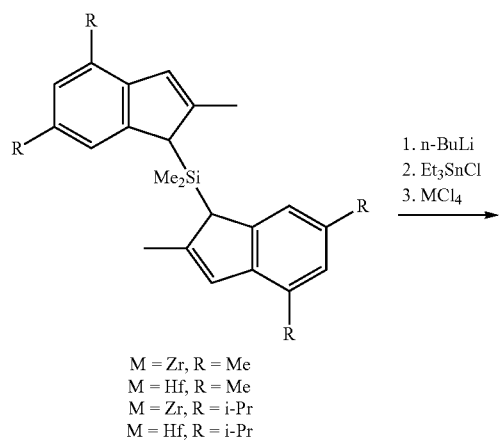

1. n-BuLi
2. Et$_3$SnCl
3. MCl$_4$

M = Zr, R = Me
M = Hf, R = Me
M = Zr, R = i-Pr
M = Hf, R = i-Pr

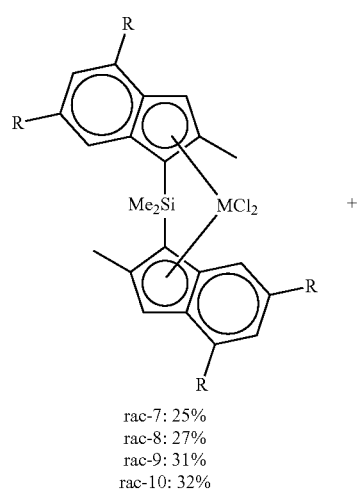

+ rac-7: 25%
rac-8: 27%
rac-9: 31%
rac-10: 32%

EP 1 209 165 A2 and U.S. Pat. No. 5,739,366 disclose diphenyl silyl bis(4-isopropyl-2,7-dimethylindenyl) ZrCl$_2$.

U.S. Pat. No. 5,767,033 mentions dimethylsilyl-bis{1-(2-methyl-4-i-propyl-7-methylindenyl)}hafnium dichloride at column 11, line 43 and uses rac-dimethylsilyl-bis{1-(2,7-dimethyl-4-isopropylindenyl)}zirconium dichloride and rac-diphenylsilyl-bis {1-(2,7-dimethyl-4-isopropylindenyl)}zirconium dichloride in the examples. Cyclic bridging groups do not appear to be mentioned.

None of the above disclose hafnium based indenyl metallocene compounds where the 4 position is substituted, the 2 and 3 positions are not substituted, and the bridge is a cyclic group, preferably used in combination with a non-coordinating anion activator.

There is still a need in the art for new and improved catalyst systems for the polymerization of olefins, in order to achieve specific polymer properties, such as high melting point, high molecular weights, to increase conversion or comonomer incorporation, to alter comonomer distribution without negatively impacting the resulting polymer's properties, increasing vinyl chain ends, particularly increasing vinyl unsaturations at the chain end while also maintaining or increasing Mw.

It is therefore an object of the present invention to provide novel catalyst compounds, catalysts systems comprising such compounds, and processes for the polymerization of olefins using such compounds and systems.

SUMMARY OF THE INVENTION

This invention relates to novel bridged hafnium transition metal metallocene catalyst compounds having two indenyl ligands substituted at the 4 position and optionally in the 7 position with a $C_1$ to $C_{10}$ alkyl, where the 2 and 3 positions are hydrogen (assuming the bridge position is counted as the one position) and the bridging atom is carbon or silicon which is incorporated into a cyclic group comprising 3, 4, 5, or 6 silicon and/or carbon atoms that make up the cyclic ring.

This invention relates to a process for producing copolymers comprising ethylene, a cyclic olefin monomer, and optionally one or more $C_3$ to $C_{12}$ alpha olefins, said process comprising contacting ethylene, a cyclic olefin monomer, and optionally one or more $C_3$ to $C_{12}$ alpha-olefins with a catalyst system comprising activator and a metallocene catalyst compound represented by the formula:

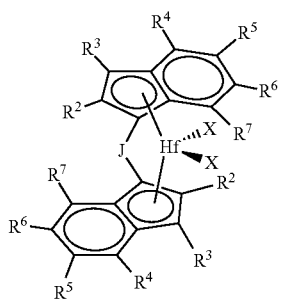

where each $R^3$ and $R^2$ is hydrogen; each $R^4$ is independently a $C_1$-$C_{10}$ alkyl; each $R^5$, $R^6$, and $R^7$ is independently hydrogen, $C_1$-$C_{50}$ substituted or unsubstituted hydrocarbyl, or $C_1$-$C_{50}$ substituted or unsubstituted halocarbyl; and $R^4$ and $R^5$, $R^5$ and $R^6$, and/or $R^6$ and $R^7$ may optionally be bonded together to form a ring structure; J is a bridging group represented by the formula $R^a{}_2 J$, where J is C or Si, and each $R^a$ is, independently, $C_1$ to $C_{20}$ substituted or unsubstituted hydrocarbyl, and the two $R^a$ form a cyclic structure incorporating J and the cyclic structure may be a saturated or partially saturated cyclic or fused ring system; and each X is a univalent anionic ligand, or two Xs are joined and bound to the metal atom to form a metallocycle ring, or two Xs are joined to form a chelating ligand, a diene ligand, or an alkylidene ligand.

In a preferred embodiment, each $R^3$ and $R^2$ is hydrogen, and each $R^4$ and $R^7$ is independently a $C_1$-$C_{10}$ alkyl.

This invention further relates to a catalyst system comprising said metallocene catalyst compound(s) and an activator.

This invention further relates to ethylene-cyclic-olefin copolymer and ethylene-alpha-olefin-cyclic-olefin copolymer compositions produced by the methods described herein.

BRIEF DESCRIPTION OF THE FIGURES

FIG. 1 is a graph of polymer Mn vs. calculated wt % ENB for the experiments in Table 1. Numbers identifying markers correspond to the Cat-ID number.

DEFINITIONS

As used herein, the numbering scheme for the Periodic Table Groups is the new notation as set out in CHEMICAL AND ENGINEERING NEWS, 63(5), 27 (1985). Therefore, a "group 4 metal" is an element from group 4 of the Periodic Table, e.g., Zr, Ti, and Hf.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be a radical, which contains hydrogen atoms and up to 50 carbon atoms and which may be linear, branched, or cyclic, and when cyclic, aromatic or non-aromatic.

Substituted hydrocarbyl radicals are radicals in which at least one hydrogen atom has been substituted with at least one functional group such as $NR^*{}_2$, $OR^*$, $SeR^*$, $TeR^*$, $PR^*{}_2$, $AsR^*{}_2$, $SbR^*{}_2$, $SR^*$, $BR^*{}_2$, $SiR^*{}_3$, $GeR^*{}_3$, $SnR^*{}_3$, $PbR^*{}_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g., F, Cl, Br, I) or halogen-containing group (e.g., $CF_3$).

Substituted halocarbyl radicals are radicals in which at least one halocarbyl hydrogen or halogen atom has been substituted with at least one functional group such as $NR^*{}_2$, $OR^*$, $SeR^*$, $TeR^*$, $PR^*{}_2$, $AsR^*{}_2$, $SbR^*{}_2$, $SR^*$, $BR^*{}_2$, $SiR^*{}_3$, $GeR^*{}_3$, $SnR^*{}_3$, $PbR^*{}_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

In some embodiments of the invention, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, butylphenyl, dibutylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compounds having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For nomenclature purposes, the following numbering schemes are used for indenyl. It should be noted that indenyl can be considered a cyclopentadienyl with fused a benzene ring. The structure below is drawn and named as an anion.

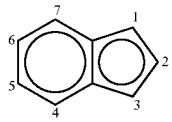

Indenyl

The following ring structures are substituted indenyls, where the substitution at the 5 and 6 positions forms a ring structure. For specific compound nomenclature purposes, these ligands are described below. A similar numbering and nomenclature scheme is used for these types of substituted indenyls that include indacenyls, cyclopenta[b]naphthalenyls, heterocyclopentanaphthyls, heterocyclopentaindenyls, and the like, as illustrated below. Each structure is drawn and named as an anion.

Non-limiting examples of indacenyls and cyclopenta[b]naphthalenyls include:

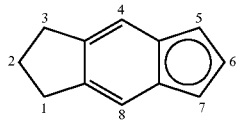

1,2,3-trihydro-s-indacenyl

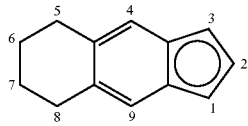

5,6,7,8-tetrahydro-cyclopenta[b]naphthalenyl

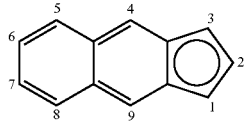

cyclopenta[b]naphthalenyl

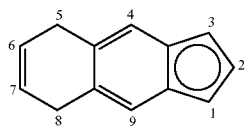

5,8-dihydro-cyclopenta[b]naphthalenyl

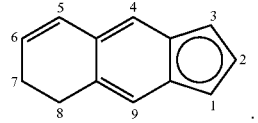

7,8-dihydro-cyclopenta[b]naphthalenyl

Non-limiting examples of heterocyclopentanaphthyls include:

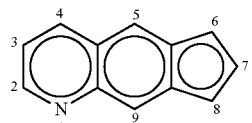

cyclopenta[g]quinolyl

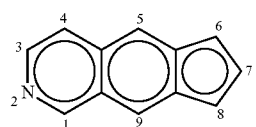

cyclopenta[g]isoquinolyl

Further non-limiting examples of heterocyclopentanaphthyls include cyclopenta[g]phosphinolyl, cyclopenta[g]isophosphinolyl, cyclopenta[g]arsinolyl, and cyclopenta[g]isoarsinolyl.

Non-limiting examples of heterocyclopentaindenyls include:

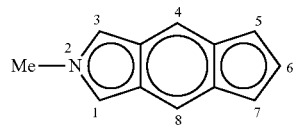

2-methylcyclopenta[f]isoindolyl

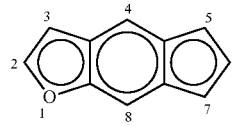 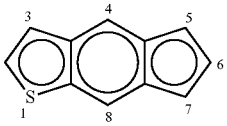

indeno[5,6-b]furyl        indeno[5,6-b]thienyl

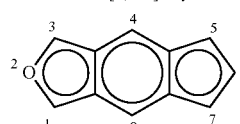 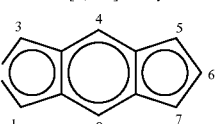

indeno[5,6-c]furyl        indeno[5,6-c]thienyl

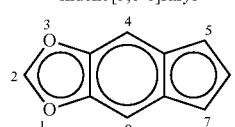 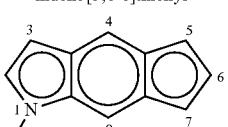

indeno[5,6-d][1,3]dioxolyl    1-methylcyclopenta[f]indolyl

Further non-limiting examples of heterocyclopentaindenyls include 1-hydrocarbylcyclopenta[f]phosphindolyl, 2-hydrocarbylcyclopenta[f]isophosphindolyl, 1-hydrocarbylcyclopenta[f]arsindolyl, 2-hydrocarbylcyclopenta[f]isoarsindolyl, indeno[5,6-b]selenophenyl, indeno[5,6-b]tellurophenyl, indeno[5,6-c]selenophenyl, indeno[5,6-c]tellurophenyl, 2-hydrocarbylcyclopenta[f]isoindolyl, and 1-hydrocarbylcyclopenta[f]indolyl, where hydrocarbyl is a "hydrocarbyl radical" as previously defined.

A "ring carbon atom" is a carbon atom that is part of a cyclic ring structure. By this definition, an indenyl fragment has nine ring carbon atoms. It is within the scope of the invention to replace one of more of the ring carbon atoms with a heteroatom, such as a boron atom, a Group 14 atom that is not carbon, a Group 15 atom, or a Group 16 atom. Preferred heteroatoms include boron, nitrogen, oxygen, phosphorus, and sulfur.

A "bondable ring position" is a ring position that is capable of bearing a substituent or bridging substituent. For example, indeno[5,6-c]thienyl has seven bondable ring positions (at the carbon atoms) and one non-bondable ring position (the sulfur atom).

"Ring Structure" means atoms bonded together in one or more cyclic arrangements.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An oligomer is typically a polymer having a low molecular weight (such an Mn of less than 25,000 g/mol, preferably less than 2,500 g/mol) or a low number of mer units (such as 75 mer units or less). An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

In the context of this document, "homopolymerization" would produce a polymer made from one type of monomer. For example, homopolymerization of propylene would produce homopolypropylene; homopolymerization of ethylene would produce homopolyethylene; and the like. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers.

Non-limiting examples of α-olefins include propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane.

For the purposes of this invention, ethylene shall be considered an α-olefin.

Non-limiting examples of cyclic olefins and diolefins (dienes) include cyclobutene, cyclopentene, cyclohexene, cycloheptene, cyclooctene, cyclononene, cyclodecene, cyclododecene, norbornene, 4-methylnorbornene, 3-methylcyclopentene, 4-methylcyclopentene, 3-methylcyclopentene, 4-methylcyclopentene, cyclopentadiene, cyclooctadiene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, 1,5-diallylcyclooctane norbornadiene, dicyclopentadiene, 5-ethylidene-2-norbornene, 5-methylidene-2-norbornene, vinylcyclohexene, vinylcyclopentene, vinylcyclobutene, vinylcyclooctene, 5-vinyl-2-norbornene, 7,7-dimethyl-bicyclo[2.2.1]hept-2-ene, tricyclo[4.2.1.0$^{2,5}$]nona-3,7-diene, 5,5-dimethyl-bicyclo[2.2.1]hept-2-ene, 5-ethyl-bicyclo[2.2.1]hept-2-ene, methyl-bicyclo[2.2.1]hept-2-ene, 2,3,3a,4,7,7a-hexahydro-4,7-methano-1H-indene, 5-ethenylidene-bicyclo[2.2.1]hept-2-ene, 5,6-dimethyl-bicyclo[2.2.1]hept-2-ene, and 5-ethynyl-bicyclo[2.2.1]hept-2-ene.

Non-limiting examples of vinylaromatic olefins and diolefins include styrene, para-methylstyrene, para-t-butylstyrene, vinylnaphthylene, vinyltoluene, and divinylbenzene.

Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and non-silicon atoms such as for example B, O, S, Se, Te, N, P, Ge, Sn, Pb, As, F, Cl, Br, or I, are contemplated, where such non-carbon or non-silicon moieties are sufficiently far removed from the double bond so as not to interfere with the coordination polymerization reaction with the catalyst and so to retain the generally hydrocarbyl characteristic. By sufficiently far removed from the double bond we intend that the number of carbon atoms, or the number of carbon and silicon atoms, separating the double bond and the non-carbon or non-silicon moiety is preferably 6 or greater, e.g., 7, or 8, or 9, or 10, or 11, or 12, or 13, or 14 or more. The number of such carbon atoms, or carbon and silicon atoms, is counted from immediately adjacent to the double bond to immediately adjacent to the non-carbon or non-silicon moiety. Examples include allyltrimethylsilane, divinylsilane, 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments.

An α-olefin may also include α-olefinic macromonomers of up to 2000 mer units.

The term "catalyst system" is defined to mean a catalyst precursor/activator pair, and optional co-activator, and an optional support material. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety. For the purposes of this invention and the claims thereto, when catalyst systems are described as comprising neutral stable forms of the components, it is well understood by one of ordinary skill in the art, that the ionic form of the component is the form that reacts with the monomers to produce polymers.

A transition metal compound may be neutral as in a precatalyst, or a charged species with a counter ion as in an activated catalyst system.

Catalyst precursor is also often referred to as precatalyst, catalyst, catalyst compound, catalyst precursor, transition metal compound or transition metal complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound.

A polymerization catalyst system is a catalyst system that can polymerize monomers to polymer. An "anionic ligand" is a negatively charged ligand which donates one or more pairs of electrons to a metal ion. A "neutral donor ligand" is a neutrally charged ligand which donates one or more pairs of electrons to a metal ion.

A metallocene catalyst is defined as an organometallic compound with at least one π-bound cyclopentadienyl moiety (or substituted cyclopentadienyl moiety such as indenyl) and more frequently two π-bound cyclopentadienyl moieties or substituted cyclopentadienyl moieties.

Non-coordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the non-coordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn. Unless otherwise noted, all molecular weight units (e.g., Mw, Mn, Mz) are g/mol. The following abbreviations may be used herein: Me is methyl, Et is ethyl, Pr is propyl, cPr is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn or Bz is benzyl, THF or thf is tetrahydrofuran, MAO is methylalumoxane.

The term "continuous" means a system that operates without interruption or cessation. For example a continuous process to produce a polymer would be one where the reactants are continually introduced into one or more reactors and polymer product is continually withdrawn.

For purposes of this invention and claims thereto, "alkoxides" include those where the alkyl group is a $C_1$ to $C_{10}$ hydrocarbyl. The alkyl group may be straight chain, branched, or cyclic.

For purposes of this invention, an "alkyl" group is a linear, branched, or cyclic radical of carbon and hydrogen. In a preferred embodiment, "alkyl" refers to linear alkyls.

Room temperature is 22° C., unless otherwise indicated.

DETAILED DESCRIPTION

Metallocene Catalyst Compounds

This invention relates to novel bridged a hafnium transition metal metallocene catalyst compounds having two indenyl ligands substituted at the 4 position (preferably at the 4 and 7 positions with a $C_1$ to $C_{10}$ alkyl, where the 2 and 3 positions are hydrogen (assuming the bridge position is counted as the one position) and the bridge is carbon or silicon which is incorporated into a cyclic group comprising 3, 4, 5 or 6 silicon and/or carbon atoms that make up the cyclic ring, preferably the 4, 7 positions, 4, 5, 7 positions, 4, 6, 7 positions, or 4, 5, 6, 7 positions are substituted, preferably by a $C_1$ to $C_{10}$ alkyl group, and optionally, if alkyl substituted, the 4 and 5, 5 and 6, and/or 6 and 7 positions may be bonded together to form a ring structure.

In a preferred embodiment, this invention is related to metallocene catalyst compounds, and catalyst systems comprising such compounds, represented by the formula (I):

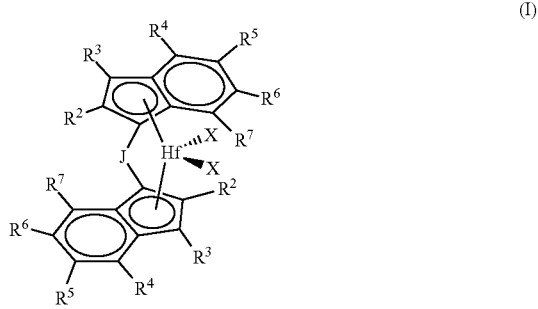

where each $R^2$ and $R^3$ is hydrogen; each $R^4$ (preferably each $R^4$ and $R^7$) is independently a $C_1$-$C_{10}$ alkyl (preferably methyl, ethyl, propyl, butyl, pentyl, heptyl, hexyl, octyl, nonyl, decyl or an isomer thereof); each $R^5$, $R^6$, and $R^7$ are independently hydrogen, or $C_1$-$C_{50}$ substituted or unsubstituted hydrocarbyl (preferably hydrogen, methyl, ethyl, propyl, butyl, pentyl, heptyl, hexyl, octyl, nonyl, decyl or an isomer thereof); and $R^4$ and $R^5$, $R^5$ and $R^6$ and/or $R^6$ and $R^7$ may optionally be bonded together to form a ring structure; J is a bridging group represented by the formula $R^a{}_2J$, where J is C or Si, and each $R^a$ is, independently $C_1$ to $C_{20}$ substituted or unsubstituted hydrocarbyl (preferably methyl, ethyl, propyl, butyl, pentyl, heptyl, hexyl, octyl, nonyl, decyl or an isomer thereof), and two $R^a$ form a cyclic structure incorporating J and the cyclic structure may be a saturated or partially saturated cyclic or fused ring system; and each X is a univalent anionic ligand, or two Xs are joined and bound to the metal atom to form a metallocycle ring, or two Xs are joined to form a chelating ligand, a diene ligand, or an alkylidene ligand.

In a preferred embodiment of the invention, each $R^4$ is, independently, a $C_1$ to $C_{10}$ alkyl group, preferably methyl, ethyl, propyl, butyl, pentyl, heptyl, hexyl, octyl, nonyl, decyl or an isomer thereof, and $R^7$ is hydrogen In a preferred embodiment of the invention, each $R^4$ and $R^7$ are, independently, a $C_1$ to $C_{10}$ alkyl group, preferably methyl, ethyl, propyl, butyl, pentyl, heptyl, hexyl, octyl, nonyl, decyl or an isomer thereof. Each $R^4$ and $R^7$ may be the same or different.

In a preferred embodiment of the invention, each $R^4$, $R^5$, and $R^7$ are, independently, a $C_1$ to $C_{10}$ alkyl group, preferably methyl, ethyl, propyl, butyl, pentyl, heptyl, hexyl, octyl, nonyl, decyl or an isomer thereof. Each, $R^4$, $R^5$, and $R^7$ may be the same or different.

In a preferred embodiment of the invention, each $R^4$, $R^6$, and $R^7$ are, independently, a $C_1$ to $C_{10}$ alkyl group, preferably methyl, ethyl, propyl, butyl, pentyl, heptyl, hexyl, octyl, nonyl, decyl or an isomer thereof. Each $R^4$, $R^6$, and $R^7$ may be the same or different.

In a preferred embodiment of the invention, each $R^4$, $R^5$, $R^6$, and $R^7$ are, independently, a $C_1$ to $C_{10}$ alkyl group, preferably methyl, ethyl, propyl, butyl, pentyl, heptyl, hexyl, octyl, nonyl, decyl or an isomer thereof. Each $R^4$, $R^5$, $R^6$, and $R^7$ may be the same or different.

In a preferred embodiment of the invention, each $R^4$ and $R^7$ are the same and are selected from the group consisting of $C_1$ to $C_{10}$ alkyl group, preferably methyl, ethyl, propyl, butyl, pentyl, heptyl, hexyl, octyl, nonyl, decyl and isomers thereof.

In a preferred embodiment of the invention, each $R^4$ and $R^7$ are the same and are selected from the group consisting of $C_1$ to $C_5$ alkyl group, preferably methyl, ethyl, propyl, butyl, pentyl, and isomers thereof.

In a preferred embodiment of the invention, each $R^4$ is independently a $C_1$ to $C_4$ alkyl group, preferably methyl, ethyl, propyl, butyl and isomers thereof.

In a preferred embodiment of the invention, each $R^4$ is independently a $C_1$ to $C_4$ alkyl group, preferably methyl, ethyl, n-propyl, cyclopropyl, or n-butyl.

In a preferred embodiment of the invention, each $R^4$ and $R^7$ are, independently, a $C_1$ to $C_4$ alkyl group, preferably methyl, ethyl, propyl, butyl and isomers thereof.

In a preferred embodiment of the invention, each $R^4$ and $R^7$ are, independently, a $C_1$ to $C_4$ alkyl group, preferably methyl, ethyl, n-propyl, cyclopropyl, or n-butyl.

In a preferred embodiment of the invention, each $R^5$ and $R^6$ are independently a $C_1$ to $C_{10}$ alkyl group, preferably methyl, ethyl, propyl, butyl, pentyl, heptyl, hexyl, octyl, nonyl, decyl or an isomer thereof, and $R^5$ and $R^6$ may optionally be bonded together to form a substituted or unsubstituted ring structure.

In a preferred embodiment of the invention, each $R^5$ and $R^6$ are independently a $C_1$ to $C_5$ alkyl group, preferably methyl, ethyl, propyl, butyl, pentyl, or an isomer thereof, and $R^5$ and $R^6$ may optionally be bonded together to form a substituted or unsubstituted ring structure.

In a preferred embodiment of the invention, each $R^4$ is independently a $C_1$ to $C_3$ alkyl group, preferably methyl, ethyl, n-propyl, isopropyl or cyclopropyl, each $R^2$, $R^3$, $R^5$, $R^6$, and $R^7$ is hydrogen.

In a preferred embodiment of the invention, each $R^4$ and $R^7$ is independently a $C_1$ to $C_3$ alkyl group, preferably methyl, ethyl, n-propyl, isopropyl or cyclopropyl, each $R^2$, $R^3$, $R^5$, and $R^6$ is hydrogen.

In a preferred embodiment of the invention, each $R^4$, $R^5$, $R^6$ and $R^7$ are, independently, a $C_1$ to $C_{10}$ alkyl group, preferably methyl, ethyl, propyl, butyl, pentyl, heptyl, hexyl, octyl, nonyl, decyl or an isomer thereof, $R^2$ and $R^3$ are hydrogen, and $R^5$ and $R^6$ are joined together to form a 5-membered ring structure.

In a preferred embodiment of the invention, each $R^4$, and $R^7$ are independently methyl, ethyl, or n-propyl, each $R^5$ and $R^6$ are independently, a $C_1$ to $C_{10}$ alkyl group, preferably methyl, ethyl, propyl, butyl, pentyl, heptyl, hexyl, octyl, nonyl, decyl or an isomer thereof, $R^2$ and $R^3$ are hydrogen, and $R^5$ and $R^6$ are joined together to form a 5-membered ring structure.

In some embodiments of the invention, the 5-membered ring structure has two adjacent $sp^2$ hybridized carbons with the remaining carbons being $sp^3$ hybridized.

In some embodiments of the invention, the 5-membered ring structure has additional $C_1$ to $C_{10}$ substituents, and wherein the substituents can be the same or different.

In some embodiments of the invention, the 5-membered ring structure has additional $C_1$ to $C_5$ substituents, and wherein the substituents can be the same or different.

In some embodiments of the invention, the 5-membered ring structure has additional $C_1$ to $C_{10}$ substituents bonded to one or more $sp^3$ hybridized carbons, and wherein the substituents can be the same or different.

In some embodiments of the invention, the 5-membered ring structure has additional $C_1$ to $C_5$ substituents bonded to one or more $sp^3$ hybridized carbons, and wherein the substituents can be the same or different.

In a preferred embodiment of the invention, each $R^4$, and $R^7$ are independently methyl, ethyl, or n-propyl, each $R^5$ and $R^6$ are independently, a $C_1$ to $C_{10}$ alkyl group, preferably methyl, ethyl, propyl, butyl, pentyl, heptyl, hexyl, octyl, nonyl, decyl or an isomer thereof, $R^2$ and $R^3$ are hydrogen, and $R^5$ and $R^6$ are joined together to form a substituted 5-membered ring structure.

In a preferred embodiment of the invention, each $R^4$ and $R^7$ are the same and are selected from the group consisting of $C_1$ to $C_3$ alkyl group, preferably methyl, ethyl, propyl, and isomers thereof, and $R^2$, $R^3$, $R^5$ and $R^6$ are hydrogen.

In a preferred embodiment of the invention, J is preferably represented by the formula:

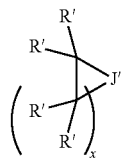

wherein J' is a carbon or silicon atom, x is 1, 2, 3, or 4, preferably 2 or 3, and each R' is, independently, hydrogen or $C_1$-$C_{10}$ hydrocarbyl, preferably hydrogen. Particularly preferred J groups include cyclopentamethylenesilylene, cyclotetramethylenesilylene, cyclotrimethylenesilylene, and the like.

In a preferred embodiment of the invention, each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system), preferably each X is independently selected from halides and $C_1$ to $C_5$ alkyl groups, preferably each X is a methyl, ethyl, propyl, butyl or pentyl group, preferably a methyl group.

In a preferred embodiment of the invention, $R^4$ is not an aryl group (substituted or unsubstituted). An aryl group is defined to be a single or multiple fused ring group where at least on ring is aromatic. A substituted aryl group is an aryl group where a hydrogen has been replaced by a heteroatom or heteroatom containing group. Examples of aryl groups include phenyl, benzyl, carbazolyl, naphthyl, and the like.

In a preferred embodiment this invention, $R^4$ and $R^7$ are not a substituted or unsubstituted aryl group.

In a preferred embodiment this invention, $R^4$, $R^5$, $R^6$ and $R^7$ are not a substituted or unsubstituted aryl group.

In some embodiments of the invention J may be $(R''_2J')_k$ wherein J' is independently carbon or silicon, k is 1, 2, or 3 preferably 1 or 2, and each R'' is, independently, hydrogen or $C_1$-$C_{10}$ hydrocarbyl. Examples of J include dimethylsilylene, methylphenylsilylene, ethylene, methylene and the like.

In a preferred embodiment of the invention, in Formula (I) each $R^3$ is hydrogen; each $R^4$ is independently a $C_1$-$C_{10}$ alkyl; each $R^2$ is independently hydrogen; each $R^7$ is independently $C_1$-$C_{10}$ alkyl; each $R^5$ and $R^6$ is independently hydrogen, $C_1$-$C_{50}$ substituted or unsubstituted hydrocarbyl, or $C_1$-$C_{50}$ substituted or unsubstituted halocarbyl; and $R^4$ and $R^5$, $R^5$ and $R^6$ and/or $R^6$ and $R^7$ may optionally be bonded together to form a ring structure; J is a bridging group represented by the formula $R^a_2J$, where J is C or Si, and each $R^a$ is, independently, $C_1$ to $C_{20}$ substituted or unsubstituted hydrocarbyl, and the two $R^a$ form a cyclic structure incorporating J and the cyclic structure may be a saturated or partially saturated cyclic or fused ring system; and each X is a univalent anionic ligand, or two Xs are joined and bound to the metal atom to form a metallocycle ring, or two Xs are joined to form a chelating ligand, a diene ligand, or an alkylidene ligand.

In a preferred embodiment, this invention is related to metallocene catalyst compounds, and catalyst systems comprising such compounds, represented by the formula (II):

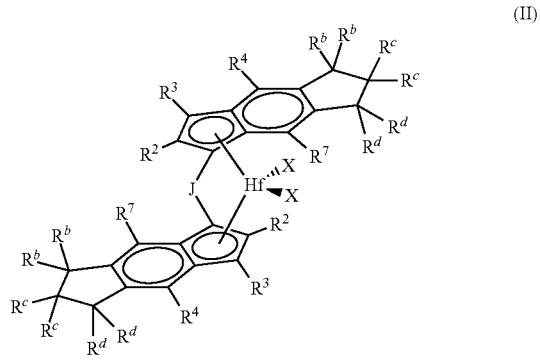

(II)

wherein each $R^2$ and $R^3$ is hydrogen; $R^4$, $R^7$, J and X are as defined above; and each $R^b$, $R^c$, and $R^d$ is independently hydrogen or a $C_1$ to $C_{10}$ hydrocarbyl.

In some embodiments of the invention, each $R^b$, $R^c$, and $R^d$ is independently hydrogen or a $C_1$ to $C_{10}$ alkyl.

In some embodiments of the invention, each $R^b$, $R^c$, and $R^d$ is independently hydrogen or a $C_1$ to $C_5$ alkyl.

In some embodiments of the invention, each $R^b$, $R^c$, and $R^d$ is independently hydrogen, methyl, ethyl, n-propyl, isopropyl, n-butyl, isobutyl, sec-butyl or tert-butyl.

In some embodiments of the invention, each $R^b$ and $R^d$ is hydrogen and each $R^c$ is independently hydrogen or a $C_1$ to $C_{10}$ alkyl.

In some embodiments of the invention, each $R^b$ and $R^d$ is hydrogen and each $R^c$ is independently a $C_1$ to $C_{10}$ alkyl.

In some embodiments of the invention, each $R^b$ and $R^d$ is hydrogen and each $R^c$ is independently hydrogen, methyl, ethyl, n-propyl, isopropyl, n-butyl, isobutyl, sec-butyl or tert-butyl.

In some embodiments of the invention, each $R^b$, and $R^d$ are hydrogen and each $R^c$ is independently methyl, ethyl, n-propyl, isopropyl, n-butyl, isobutyl, sec-butyl or tert-butyl.

In some embodiments of the invention, each $R^b$ and $R^d$ is hydrogen and both $R^c$ are a $C_1$ to $C_{10}$ alkyl.

In some embodiments of the invention, each $R^b$ and $R^d$ is hydrogen and both $R^c$ are methyl, ethyl, n-propyl, isopropyl, n-butyl, isobutyl, sec-butyl or tert-butyl.

In some embodiments of the invention, each $R^b$ and $R^d$ is hydrogen and both $R^c$ are methyl, ethyl, or n-propyl.

In some embodiments of the invention, each $R^b$ and $R^d$ is hydrogen and both $R^c$ are methyl.

Metallocene compounds that are particularly useful in this invention include one or more of:
cyclotetramethylenesilylene-bis(4,7-dimethylinden-1-yl) hafnium dimethyl,
cyclopentamethylenesilylene-bis(4,7-dimethylinden-1-yl) hafnium dimethyl,
cyclotrimethylenesilylene-bis(4,7-dimethylinden-1-yl)hafnium dimethyl,
cyclotetramethylenesilylene-bis(4,7-dimethylinden-1-yl) hafnium dichloride,
cyclopentamethylenesilylene-bis(4,7-dimethylinden-1-yl) hafnium dichloride,
cyclotrimethylenesilylene-bis(4,7-dimethylinden-1-yl)hafnium dichloride,
cyclotetramethylenesilylene-bis(4,7-diethylinden-1-yl)hafnium dimethyl,
cyclopentamethylenesilylene-bis(4,7-diethylinden-1-yl)hafnium dimethyl,
cyclotrimethylenesilylene-bis(4,7-diethylinden-1-yl)hafnium dimethyl,
cyclotetramethylenesilylene-bis(4,7-diethylinden-1-yl)hafnium dichloride,
cyclopentamethylenesilylene-bis(4,7-diethylinden-1-yl)hafnium dichloride,
cyclotrimethylenesilylene-bis(4,7-diethylinden-1-yl)hafnium dichloride,
cyclotetramethylenesilylene-bis(4,8-dimethyl-1,2,3-trihydro-s-indacen-5-yl)hafnium dimethyl,
cyclopentamethylenesilylene-bis(4,8-dimethyl-1,2,3-trihydro-s-indacen-5-yl)hafnium dimethyl,
cyclotrimethylenesilylene-bis(4,8-dimethyl-1,2,3-trihydro-s-indacen-5-yl)hafnium dimethyl,
cyclotetramethylenesilylene-bis(4,8-dimethyl-1,2,3-trihydro-s-indacen-5-yl)hafnium dichloride,
cyclopentamethylenesilylene-bis(4,8-dimethyl-1,2,3-trihydro-s-indacen-5-yl)hafnium dichloride, cyclotrimethylenesilylene-bis(4,8-dimethyl-1,2,3-trihydro-s-indacen-5-yl)hafnium dichloride,
cyclotetramethylenesilylene-bis(4,8-diethyl-1,2,3-trihydro-s-indacen-5-yl)hafnium dimethyl,
cyclopentamethylenesilylene-bis(4,8-diethyl-1,2,3-trihydro-s-indacen-5-yl)hafnium dimethyl,
cyclotrimethylenesilylene-bis(4,8-diethyl-1,2,3-trihydro-s-indacen-5-yl)hafnium dimethyl,
cyclotetramethylenesilylene-bis(4,8-diethyl-1,2,3-trihydro-s-indacen-5-yl)hafnium dichloride,
cyclopentamethylenesilylene-bis(4,8-diethyl-1,2,3-trihydro-s-indacen-5-yl)hafnium dichloride, and
cyclotrimethylenesilylene-bis(4,8-diethyl-1,2,3-trihydro-s-indacen-5-yl)hafnium dichloride.

In some embodiments of the invention, useful catalysts include: dimethylsilylene-bis(4,7-dimethylinden-1-yl)hafnium dimethyl, ethylene-bis(4,7-dimethylinden-1-yl)hafnium dimethyl, dimethylsilylene-bis(4,7-diethylinden-1-yl)hafnium dimethyl, and/or ethylene-bis(4,7-diethylinden-1-yl)hafnium dimethyl.

In a preferred embodiment, the hafnium dimethyl in any of the compounds listed above may be replaced with hafnium dialkyl (such as diethyl, dipropyl, diphenyl, dibenzyl) or a dihalide (such as difluoride, dibromide, or diiodide). In a preferred embodiment of the invention, the catalyst compound is in the rac form. In a preferred embodiment of the invention, at least 90 wt % of the catalyst compound is in the rac form, based upon the weight of the rac and meso forms present, preferably from 92 to 100 wt %, preferably from 95 to 100 wt %, preferably from 98 to 100 wt %. In a preferred embodiment of the invention, the ratio of rac to meso in the catalyst compound is from 1:100 to 100:1, preferably 1:1 to 100:1, preferably 50:1 to 100:1, preferably 85:1 to 100:1. In a preferred embodiment of the invention, the catalyst compound is greater than 90% rac, preferably greater than 95% rac, preferably greater than 98% rac.

Amounts of rac and meso isomers are determined by proton NMR. $^1$H NMR data are collected at ambient temperature (22° C.) in a 5 mm probe using a 400 MHz Bruker spectrometer with deuterated solvent in which the precatalyst compound is completely soluble. Data is recorded using a maximum pulse width of 45°, 8 seconds between pulses and signal averaging 16 transients.

In a preferred embodiment in any of the processes described herein one metallocene catalyst compound is used, e.g., the metallocene catalyst compounds are not different. For purposes of this invention one metallocene catalyst compound is considered different from another if they differ by at least one atom. For example "bis-indenyl zirconium dichloride" is different from (indenyl)(2-methylindenyl) zirconium dichloride" which is different from "(indenyl)(2-methylindenyl) hafnium dichloride." Metallocene catalyst compounds that differ only by isomer are considered the same for purposes of determining whether they are the "same", e.g., rac-dimethylsilylbis(2-methyl-4-propyl)hafnium dimethyl and meso-dimethylsilylbis(2-methyl-4-propyl)hafnium dimethyl are isomers of dimethylsilylbis(2-methyl-4-propyl)hafnium dimethyl. Furthermore for hafnium compounds, the Zr analog may be present at up to 3 wt % and still be considered the "same." Preferably, the zirconium analog is present at less than 2 wt % Zr, more preferably less than 1 wt % Zr, even more preferably less than 0.5 wt % Zr, more preferably less than 0.1 wt %. Amount of Zr and Hf present is determined by using ICPES (Inductively Coupled Plasma Emission Spectrometry), which is described in J. W. Olesik, "Inductively Coupled Plasma-Optical Emission Spectroscopy," in Encyclopedia of Materials Characterization, C. R. Brundle, C. A. Evans, Jr. and S. Wilson, eds., Butterworth-Heinemann, Boston, Mass., 1992, pp. 633-644).

In some embodiments, two or more different metallocene catalyst compounds are present in the catalyst system used herein. In some embodiments, two or more different metallocene catalyst compounds are present in the reaction zone where the process(es) described herein occur. When two transition metal compound based catalysts are used in one reactor as a mixed catalyst system, the two transition metal compounds should be chosen such that the two are compatible. A simple screening method such as by $^1$H or $^{13}$C NMR, known to those of ordinary skill in the art, can be used to determine which transition metal compounds are compatible. It is preferable to use the same activator for the transition metal compounds, however, two different activators, such as a non-coordinating anion activator and an alumoxane, can be used in combination. If one or more transition metal compounds contain an X ligand which is not a hydride, hydrocarbyl, or substituted hydrocarbyl, then the alumoxane or aluminum alkyl (such as triisobutyl aluminum) are typically contacted with the transition metal compounds prior to addition of the non-coordinating anion activator.

The two transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10 to 99.9% A to 0.1 to 90% B, alternatively 25 to 99% A to 0.5 to 50% B, alternatively 50 to 99% A to 1 to 25% B, and alternatively 75 to 99% A to 1 to 10% B.

In a preferred embodiment, the hafnium bis-indenyl metallocene compound used herein is at least 90% rac isomer and is the indenyl groups are substituted at the 4 position with a $C_1$ to $C_{10}$ alkyl group, the 2 and 3 positions are hydrogen, the bridge is carbon or silicon which is incorporated into a 4, 5 or 6 membered ring.

The metallocene compounds described herein are synthesized according to procedures known in the art.

Activators

The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing non-coordinating or weakly coordinating anion.

In one embodiment, alumoxane activators are utilized as an activator in the catalyst composition. Alumoxanes are generally oligomeric compounds containing —Al($R^1$)—O— sub-units, where $R^1$ is an alkyl group. Examples of alumoxanes include methylalumoxane (MAO), modified methylalumoxane (MMAO), ethylalumoxane and isobutyl-alumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

When the activator is an alumoxane (modified or unmodified), some embodiments select the maximum amount of activator at a 5000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mole %, alternately the alumoxane is present at a molar ratio of aluminum to catalyst compound transition metal less than 500:1, preferably less than 300:1, preferably less than 100:1, preferably less than 1:1.

The term "non-coordinating anion" (NCA) means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium, and indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral stoichiometric activator is tris perfluorophenyl boron or tris perfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP 0 570 982 A; EP 0 520 732 A; EP 0 495 375 A; EP 0 500 944 B1; EP 0 277 003 A; EP 0 277 004 A; U.S. Pat. Nos. 5,153,157; 5,198,401; 5,066,741; 5,206,197; 5,241,025; 5,384,299; 5,502,124; and U.S. patent application Ser. No. 08/285,380, filed Aug. 3, 1994; all of which are herein fully incorporated by reference.

Preferred compounds useful as an activator in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic, diolefinic and acetylenically unsaturated substrates or other neutral Lewis bases, such as ethers, amines, and the like. Two classes of useful compatible non-coordinating anions have been disclosed in EP 0 277, 003 A1, and EP 0 277,004 A1: 1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment, the stoichiometric activators include a cation and an anion component, and are preferably represented by the following formula (1):

$$(Z)_d^+(A^{d-}) \qquad (1)$$

wherein Z is (L-H) or a reducible Lewis Acid, L is an neutral Lewis base; H is hydrogen; $(L-H)^+$ is a Bronsted acid; $A^{d-}$ is a non-coordinating anion having the charge d−; and d is an integer from 1 to 3.

When Z is (L-H) such that the cation component is $(L-H)_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation $(L-H)_d^+$ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid it is preferably represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid is represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl. In a preferred embodiment, the reducible Lewis acid is triphenyl carbenium.

The anion component $A^{d-}$ include those having the formula $[M^{k+}Q_n]^{d-}$ wherein k is 1, 2, or 3; n is 1, 2, 3, 4, 5, or 6, preferably 3, 4, 5 or 6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoro aryl group. Examples of suitable $A^{d-}$ components also include diboron compounds as disclosed in U.S. Pat. No. 5,447,895, which is fully incorporated herein by reference.

In a preferred embodiment, this invention relates to a method to polymerize olefins comprising contacting olefins (preferably ethylene) with metallocene catalyst compound described herein, a chain transfer agent and a boron containing NCA activator represented by the formula (2):

$$Z_d^+(A^{d-}) \quad (2)$$

where: Z is (L-H) or a reducible Lewis acid; L is an neutral Lewis base (as further described above); H is hydrogen; (L-H) is a Bronsted acid (as further described above); $A^{d-}$ is a boron containing non-coordinating anion having the charge d (as further described above); d is 1, 2, or 3.

In a preferred embodiment in any NCA's represented by Formula 2 described above, the reducible Lewis acid is represented by the formula: $(Ar_3C^+)$, where Ar is aryl or aryl substituted with a heteroatom, a $C_1$ to $C_{40}$ hydrocarbyl, or a substituted C1 to C40 hydrocarbyl, preferably the reducible Lewis acid is represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's represented by Formula 2 described above, $Z_d^+$ is represented by the formula: $(L-H)_d^+$, wherein L is an neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

In a preferred embodiment in any of the NCA's represented by Formula 2 described above, the anion component $A^{d-}$ is represented by the formula $[M^{*k*+}Q^*_{n*}]_{d*-}$ wherein k* is 1, 2, or 3; n* is 1, 2, 3, 4, 5, or 6 (preferably 1, 2, 3, or 4); n*−k*=d*; M* is boron; and Q* is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q* having up to 20 carbon atoms with the proviso that in not more than 1 occurrence is Q* a halide.

This invention also relates to a method to polymerize olefins comprising contacting olefins (such as ethylene) with a metallocene catalyst compound described herein, a chain transfer agent and an NCA activator represented by the formula (3):

$$R_nM^{**}(ArNHal)_{4-n} \quad (3)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula 3 also comprises a suitable cation that is essentially non-interfering with the ionic catalyst complexes formed with the transition metal compounds, preferably the cation is $Z_d^+$ as described above.

In a preferred embodiment in any of the NCA's comprising an anion represented by Formula 3 described above, R is selected from the group consisting of substituted or unsubstituted $C_1$ to $C_{30}$ hydrocarbyl aliphatic or aromatic groups, where substituted means that at least one hydrogen on a carbon atom is replaced with a hydrocarbyl, halide, halocarbyl, hydrocarbyl or halocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl groups; —$SR^1$, —$NR^2_2$, and —$PR^3_2$, where each $R^1$, $R^2$, or $R^3$ is independently a substituted or unsubstituted hydrocarbyl as defined above; or a $C_1$ to $C_{30}$ hydrocarbyl substituted organometalloid.

In a preferred embodiment in any of the NCA's comprising an anion represented by Formula 3 described above, the NCA also comprises cation comprising a reducible Lewis acid represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's comprising an anion represented by Formula 3 described above, the NCA also comprises a cation represented by the formula, $(L-H)_d^+$, wherein L is an neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

Further examples of useful activators include those disclosed in U.S. Pat. Nos. 7,297,653 and 7,799,879.

Another activator useful herein comprises a salt of a cationic oxidizing agent and a non-coordinating, compatible anion represented by the formula (4):

$$(OX^{e+})_d(A^{d-})_e \quad (4)$$

wherein $OX^{e+}$ is a cationic oxidizing agent having a charge of e+; e is 1, 2, or 3; d is 1, 2 or 3; and $A^{d-}$ is a non-coordinating anion having the charge of d− (as further described above). Examples of cationic oxidizing agents include: ferrocenium, hydrocarbyl-substituted ferrocenium, $Ag^+$, or $Pb^{+2}$. Preferred embodiments of $A^{d-}$ include tetrakis (pentafluorophenyl)borate.

In another embodiment, metallocene catalyst compounds described herein can be used with Bulky activators. A "Bulky activator" as used herein refers to anionic activators represented by the formula:

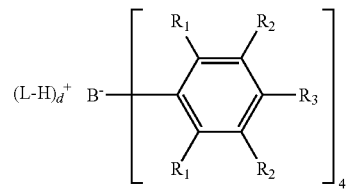

where:
each $R_1$ is, independently, a halide, preferably a fluoride;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring);
L is an neutral Lewis base; $(L-H)^+$ is a Bronsted acid; d is 1, 2, or 3;
wherein the anion has a molecular weight of greater than 1020 g/mol; and
wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_S$, where $V_S$ is the scaled volume. $V_S$ is the sum of the relative volumes of the constituent atoms, and is calculated from the molecular formula of the substituent using the following table of relative volumes. For fused rings, the $V_S$ is decreased by 7.5% per fused ring.

| Element | Relative Volume |
|---|---|
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

Exemplary bulky substituents of activators suitable herein and their respective scaled volumes and molecular volumes are shown in the table below. The dashed bonds indicate binding to boron, as in the general formula above.

| Activator | Structure of boron substituents | Molecular Formula of each substituent | MV Per subst. (Å³) | Total MV (Å³) |
|---|---|---|---|---|
| Dimethylanilinuim tetrakis(perfluoronaphthyl)borate | | $C_{10}F_7$ | 261 | 1044 |
| Dimethylanilinium tetrakis(perfluorobiphenyl)borate | | $C_{12}F_9$ | 349 | 1396 |
| [4-tButyl-PhNMe$_2$H][($C_6F_3(C_6F_5)_2)_4$B] | | $C_{18}F_{13}$ | 515 | 2060 |

Exemplary Bulky activators useful in catalyst systems herein include: trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, [4-t-butyl-PhNMe$_2$H] [($C_6F_3(C_6F_5)_2$)$_4$B], and the types disclosed in U.S. Pat. No. 7,297,653.

Illustrative, but not limiting, examples of boron compounds which may be used as an activator in the processes of this invention are:
trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis (perfluoronaphthyl)borate, triethylammonium tetrakis (perfluoronaphthyl)borate, tripropylammonium tetrakis (perfluoronaphthyl)borate, tri(n-butyl)ammonium tetrakis (perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium) tetrakis(3,5-bis(trifluoromethyl)phenyl)borate, and dialkyl ammonium salts, such as: di-(i-propyl)ammonium tetrakis(pentafluorophenyl)borate, and dicyclohexylammonium tetrakis(pentafluorophenyl)borate; and additional tri-substituted phosphonium salts, such as tri(o-tolyl)phosphonium tetrakis(pentafluorophenyl)borate, and tri(2,6-dimethylphenyl)phosphonium tetrakis(pentafluorophenyl)borate.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B(C$_6$F$_5$)$_4$$^-$], [Me$_3$NH$^+$][B(C$_6$F$_5$)$_4$$^-$]; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl) phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl)borate, N,N-dialkylanilinium tetrakis-(2, 3,4,6-tetrafluorophenyl)borate, trialkylammonium tetrakis (perfluoronaphthyl)borate, N,N-dialkylanilinium tetrakis (perfluoronaphthyl)borate, trialkylammonium tetrakis (perfluorobiphenyl)borate, N,N-dialkylanilinium tetrakis (perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl) phenyl)borate, di-(i-propyl)ammonium tetrakis(penta-fluorophenyl)borate, (where alkyl is methyl, ethyl, propyl, n-butyl, sec-butyl, or t-butyl).

In a particularly preferred embodiment, the activator used in combination with any catalyst compound(s) described herein is N,N-dimethylanilinium tetrakis (perfluoronaphthyl)borate.

In a preferred embodiment, any of the activators described herein may be mixed together before or after combination with the catalyst compound, preferably before being mixed with the catalyst compound.

In some embodiments two NCA activators may be used in the polymerization and the molar ratio of the first NCA activator to the second NCA activator can be any ratio. In some embodiments, the molar ratio of the first NCA activator to the second NCA activator is 0.01:1 to 10,000:1, preferably 0.1:1 to 1000:1, preferably 1:1 to 100:1.

Further, the typical activator-to-catalyst ratio, e.g., all NCA activators-to-catalyst ratio is a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

It is also within the scope of this invention that the catalyst compounds can be combined with combinations of alumoxanes and NCA's (see for example, U.S. Pat. No. 5,153,157; U.S. Pat. No. 5,453,410; EP 0 573 120 B1; WO 94/07928, and WO 95/14044 which discuss the use of an alumoxane in combination with an ionizing activator).

Optional Scavengers or Co-Activators

In addition to the activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum and the like. Other oxophilic species such as diethyl zinc may be used.

Optional Support Materials

In embodiments herein, the catalyst system may comprise an inert support material. Preferably the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2/Al_2O_3$.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 µm. More preferably, the surface area of the support material is in the range of from about 50 to about 500 $m^2/g$, pore volume of from about 0.5 to about 3.5 cc/g and average particle size of from about 10 to about 200 µm. Most preferably the surface area of the support material is in the range is from about 100 to about 400 $m^2/g$, pore volume from about 0.8 to about 3.0 cc/g and average particle size is from about 5 to about 100 µm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 $m^2/gm$; pore volume of 1.65 $cm^3/gm$). Preferred silicas are marketed under the tradenames of DAVISON 952 or DAVISON 955 by the Davison Chemical Division of W. R. Grace and Company. In other embodiments DAVISON 948 is used.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one metallocene compound and an activator.

The support material, having reactive surface groups, typically hydroxyl groups, is slurried in a non-polar solvent and the resulting slurry is contacted with a solution of a metallocene compound and an activator. In some embodiments, the slurry of the support material is first contacted with the activator for a period of time in the range of from about 0.5 hours to about 24 hours, from about 2 hours to about 16 hours, or from about 4 hours to about 8 hours. The solution of the metallocene compound is then contacted with the isolated support/activator. In some embodiments, the supported catalyst system is generated in situ. In alternate embodiment, the slurry of the support material is first contacted with the catalyst compound for a period of time in the range of from about 0.5 hours to about 24 hours, from about 2 hours to about 16 hours, or from about 4 hours to about 8 hours. The slurry of the supported metallocene compound is then contacted with the activator solution.

The mixture of the metallocene, activator and support is heated to about 0° C. to about 70° C., preferably to about 23°

C. to about 60° C., preferably at room temperature. Contact times typically range from about 0.5 hours to about 24 hours, from about 2 hours to about 16 hours, or from about 4 hours to about 8 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polymerization Processes

In embodiments herein, the invention relates to polymerization processes where ethylene, the cyclic monomer, and optionally comonomer, are contacted with a catalyst system comprising an activator and at least one metallocene compound, as described above. The catalyst compound and activator may be combined in any order, and are combined typically prior to contacting with the monomer.

Comonomers useful herein include substituted or unsubstituted $C_3$ to $C_{40}$ alpha olefins, preferably $C_3$ to $C_{20}$ alpha olefins, preferably $C_3$ to $C_{12}$ alpha olefins, preferably propylene, butene, pentene, hexene, heptene, octene, nonene, decene, undecene, dodecene and isomers thereof.

Cyclic monomers include $C_2$ to $C_{40}$ cyclic monomers (including olefins and diolefins) may be strained or unstrained, monocyclic or polycyclic, and may optionally include heteroatoms and/or one or more functional groups. Cyclic monomers may have a single unsaturation such as cyclopentene, or more than one unsaturation such as norbornadiene.

Useful cyclic monomers include cyclobutene, cyclopentene, cyclohexene, cycloheptene, cyclooctene, cyclononene, cyclodecene, cyclododecene, norbornene, 4-methylnorbornene, 3-methylcyclopentene, 4-methylcyclopentene, cyclopentadiene, cyclooctadiene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane, norbornadiene, dicyclopentadiene, 5-ethylidene-2-norbornene, 5-methylidene-2-norbornene, vinylcyclohexene, vinylcyclopentene, vinylcyclobutene, vinylcyclooctene, 5-vinyl-2-norbornene, 7,7-dimethyl-bicyclo[2.2.1]hept-2-ene, tricyclo[4.2.1.0$^{2,5}$] nona-3,7-diene, 5,5-dimethyl-bicyclo[2.2.1]hept-2-ene, 5-ethyl-bicyclo[2.2.1]hept-2-ene, methyl-bicyclo[2.2.1] hept-2-ene, 2,3,3a,4,7,7,7a-hexahydro-4,7-methano-1H-indene, 5-ethenylidene-bicyclo[2.2.1]hept-2-ene, 5, 6-dimethyl-bicyclo[2.2.1]hept-2-ene, 5-ethynyl-bicyclo[2.2.1] hept-2-ene, 7-oxanorbornene, 7-oxanorbornadiene, and substituted derivatives thereof, and preferably norbornene, norbornadiene, dicyclopentadiene, 5-ethylidene-2-norbornene (ENB), 5-methylidene-2-norbornene, vinylcyclohexene, and 5-vinyl-2-norbornene, most preferably 5-ethylidene-2-norbornene.

In some embodiments, the cyclic monomer is preferably a cyclic diene monomer such as cyclopentadiene, cyclooctadiene, norbornadiene, dicyclopentadiene, 5-ethylidene-2-norbornene, 5-methylidene-2-norbornene, vinylcyclohexene, vinylcyclopentene, vinylcyclobutene, vinylcyclooctene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane, 5-vinyl-2-norbornene, tricyclo[4.2.1.0$^{2,5}$]nona-3,7-diene, preferably norbornadiene, dicyclopentadiene, 5-ethylidene-2-norbornene, and 5-methylidene-2-norbornene, most preferably 5-ethylidene-2-norbornene.

In another preferred embodiment, the monomer comprises ethylene, one or more cyclic monomers and an optional comonomers comprising one or more of propylene or $C_4$ to $C_{12}$ olefins. The $C_4$ to $C_{12}$ olefin monomers may be linear or branched. In another preferred embodiment, the monomer comprises ethylene, propylene and one or more cyclic monomers.

In another preferred embodiment, the monomer comprises ethylene, propylene and one or more cyclic diene.

In another preferred embodiment, the monomer comprises ethylene, propylene and 5-ethylidene-2-norbornene.

In another preferred embodiment, the monomer comprises ethylene and one or more cyclic monomers.

In another preferred embodiment, the monomer comprises ethylene and norbornene.

In a preferred embodiment, one or more cyclic monomers are present in the polymer produced herein at up to 50 weight %, preferably up to 25 weight %, preferably at 2 to 15 weight %, preferably 3 to 12 weight %, even more preferably 6 to 10 weight %, based upon the total weight of the composition.

In a preferred embodiment ENB is present in the polymer produced herein at up to 25 weight %, preferably at 2 to 15 weight %, preferably 3 to 12 weight %, even more preferably 6 to 10 weight %, based upon the total weight of the composition.

In a preferred embodiment of the polymerization process, the conversion of cyclic monomer is greater than 6%, more preferably greater than 10%, more preferably greater than 15%, most preferably greater than 20% based on the weight of cyclic monomer used in the process and the weight of cyclic monomer incorporated into the polymer.

In a preferred embodiment of the polymerization process, the conversion of ENB monomer is greater than 6%, more preferably greater than 10%, more preferably greater than 15%, most preferably greater than 20% based on the weight of ENB used in the process and the weight of ENB incorporated into the polymer.

In some embodiments, where butene is the comonomer, the butene source may be a mixed butene stream comprising various isomers of butene. The 1-butene monomers are expected to be preferentially consumed by the polymerization process. Use of such mixed butene streams will provide an economic benefit, as these mixed streams are often waste streams from refining processes, for example, $C_4$ raffinate streams, and can therefore be substantially less expensive than pure 1-butene.

When used, preferably the $C_3$ to $C_{12}$ alpha-olefins are present in the copolymer at less than 60 mol %, preferably less than 55 mol %, preferably from 1 to 55 mol %, preferably from 5 to 50 mol %, preferably from 10 to 45 mol %, preferably from 20 to 40 mol %, with the balance of the copolymer being made up of ethylene.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferred polymerizations can be run at any temperature and/or pressure suitable to obtain the desired polymers. Typical temperatures and/or pressures include a temperature in the range of from about 0° C. to about 300° C., preferably about 20° C. to about 200° C., preferably about 35° C. to about 150° C., preferably from about 40° C. to about 120° C., preferably from about 45° C. to about 80° C.; and at a pressure in the range of from about 0.35 MPa to about 200 MPa, preferably from about 1 MPa to about 70 MPa, or preferably from about 2 MPa to about 40 MPa, or preferably from about 4 MPa to about 20 MPa. In various such embodiments, pressure may range from a low of any one of about 0.1, 1, 5, and 10 to a high of any one of about 3, 5, 10, 50, 100, 150, and 200 MPa, provided the high end of the range is greater than the low end.

In a typical polymerization, the run time of the reaction is up to 300 minutes, preferably in the range of from about 5 to 250 minutes, or preferably from about 10 to 120 minutes.

In a some embodiments hydrogen is present in the polymerization reactor. When present, hydrogen is present at a partial pressure of 0.001 to 50 psig (0.007 to 345 kPa), preferably from 0.01 to 25 psig (0.07 to 172 kPa), more preferably 0.1 to 10 psig (0.7 to 70 kPa).

In an alternate embodiment, the activity of the catalyst is at least 50 g/mmol/hour, preferably 500 or more g/mmol/hour, preferably 5000 or more g/mmol/hr, preferably 50,000 or more g/mmol/hr, preferably 100,000 or more g/mmol/hr.

In an alternate embodiment, the conversion of olefin monomer is at least 10%, based upon polymer yield and the weight of the monomer entering the reaction zone, preferably 20% or more, preferably 30% or more, preferably 50% or more, preferably 80% or more.

In an embodiment of the invention, little or no alumoxane is used in the process to produce the polymers. Preferably, alumoxane is present at zero mol %, alternately the alumoxane is present at a molar ratio of aluminum to transition metal 500:1 or less, preferably 300:1 or less, preferably 100:1 or less.

In an embodiment of the invention, little or no scavenger is used in the process to produce the polymer. The scavenger may be present at a molar ratio of scavenger metal to transition metal of less than 100:1, preferably less than 50:1, preferably less than 20:1, preferably less than 10:1.

In a preferred embodiment, the polymerization: 1) is conducted at temperatures of 0 to 300° C. (preferably 25 to 150° C., preferably 40 to 130° C., preferably 70 to 120° C.); 2) is conducted at a pressure of atmospheric pressure to 40 MPa (preferably 0.35 to 16 MPa, preferably from 0.45 to 12 MPa, preferably from 0.5 to 20 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are preferably present in the solvent at less than 1 wt %, preferably less than 0.5 wt %, preferably at 0 wt % based upon the weight of the solvents) or aromatic solvents such as toluene, benzene or xylenes; 4) wherein the catalyst system used in the polymerization comprises less than 0.5 mol %, preferably 0 mol % alumoxane, alternately the alumoxane is present at a molar ratio of aluminum to transition metal 500:1 or less, preferably 300:1 or less, preferably 100:1 or less,) the polymerization preferably occurs in one reaction zone; 5) the productivity of the catalyst compound is at least 80,000 g/mmol/hr (preferably at least 150,000 g/mmol/hr, preferably at least 200,000 g/mmol/hr, preferably at least 250,000 g/mmol/hr); 6) optionally scavengers (such as trialkyl aluminum compounds) are absent (e.g., present at zero mol %, alternately the scavenger is present at a molar ratio of scavenger metal to transition metal of less than 100:1, preferably less than 50:1, preferably less than 20:1, preferably less than 10:1); and 7) optionally hydrogen is present in the polymerization reactor at a partial pressure of 0.001 to 50 psig (0.007 to 345 kPa) (preferably from 0.01 to 25 psig (0.07 to 172 kPa), more preferably 0.1 to 10 psig (0.7 to 70 kPa)). In a preferred embodiment, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone. Room temperature is 23° C. unless otherwise noted.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

In a preferred embodiment of the invention, higher reactor temperatures, such as 70 to 150° C., and Bulky activators, such N,N-dimethylanilinium tetrakis (perfluoronaphthyl) borate are used.

In a preferred embodiment of the invention, the polymerization occurs in a supercritical or supersolution state.

The terms "dense fluid" "solid-fluid phase transition temperature" "phase transition" "solid-fluid phase transition pressure" "fluid-fluid phase transition pressure" "fluid-fluid phase transition temperature" "cloud point" "cloud point pressure" "cloud point temperature" "supercritical state" "critical temperature (Tc)" "critical pressure (Pc)" "supercritical polymerization" "homogeneous polymerization" "homogeneous polymerization system" are defined in U.S. Pat. No. 7,812,104, which is incorporated by reference herein.

A supercritical polymerization means a polymerization process in which the polymerization system is in a dense (i.e. its density is 300 kg/m$^3$ or higher), supercritical state.

A super solution polymerization or supersolution polymerization system is one where the polymerization occurs at a temperature of 65° C. to 150° C. and a pressure of between 250 to 5,000 psi (1.72 to 34.5 MPa), preferably the super solution polymerization polymerizes a $C_2$ to $C_{20}$ monomer (preferably propylene), and has: 1) 0 to 20 wt % of one or more comonomers (based upon the weight of all monomers and comonomers present in the feed) selected from the group consisting of ethylene and $C_4$ to $C_{12}$ olefins and diolefins, 2) from 20 to 65 wt % diluent or solvent, based upon the total weight of feeds to the polymerization reactor, 3) 0 to 5 wt % scavenger, based upon the total weight of feeds to the polymerization reactor, 4) the olefin monomers and any comonomers are present in the polymerization system at 15 wt % or more, 5) the polymerization temperature is above the solid-fluid phase transition temperature of the polymerization system and above a pressure greater than 1 MPa below the cloud point pressure of the polymerization system, provided however that the polymerization occurs: (1) at a temperature below the critical temperature of the polymerization system, or (2) at a pressure below the critical pressure of the polymerization system.

In a preferred embodiment of the invention, the polymerization process is conducted under homogeneous (such as solution, supersolution, or supercritical) conditions preferably including a temperature of about 60° C. to about 200° C., preferably for 65° C. to 195° C., preferably for 90° C. to 190° C., preferably from greater than 100° C. to about 180° C., such as 105° C. to 170° C., preferably from about 110° C. to about 160° C. The process may conducted at a pressure in excess of 1.7 MPa, especially under supersolution conditions including a pressure of between 1.7 MPa and 30 MPa, or especially under supercritical conditions including a pressure of between 15 MPa and 1500 MPa, especially when the monomer composition comprises propylene or a mixture of propylene with at least one ethylene or $C_4$ to $C_{20}$ α-olefin. In a preferred embodiment the monomer is propylene and the propylene is present at 15 wt % or more in the polymerization system, preferably at 20 wt % or more, preferably at 30 wt % or more, preferably at 40 wt % or more, preferably at 50 wt % or more, preferably at 60 wt % or more, preferably at 70 wt % or more, preferably 80 wt % or more. In an alternate embodiment, the monomer and any comonomer present are present at 15 wt % or more in the polymerization system, preferably at 20 wt % or more, preferably at 30 wt % or more, preferably at 40 wt % or more, preferably at 50 wt % or more, preferably at 60 wt % or more, preferably at 70 wt % or more, preferably 80 wt % or more.

In a preferred embodiment of the invention, the polymerization process is conducted under supersolution conditions including temperatures from about 65° C. to about 150° C., preferably from about 75° C. to about 140° C., preferably from about 90° C. to about 140° C., more preferably from about 100° C. to about 140° C., and pressures of between 1.72 MPa and 35 MPa, preferably between 5 and 30 MPa.

In another particular embodiment of the invention, the polymerization process is conducted under supercritical conditions (preferably homogeneous supercritical conditions, e.g., above the supercritical point and above the cloud point) including temperatures from about 90° C. to about 200° C., and pressures of between 15 MPa and 1500 MPa, preferably between 20 MPa and 140 MPa.

In another embodiment, the polymerization occurs at a temperature above the solid-fluid phase transition temperature of the polymerization system and a pressure no lower than 10 MPa below the cloud point pressure (CPP) of the polymerization system (preferably no lower than 8 MPa below the CPP, preferably no lower than 6 MPa below the CPP, preferably no lower than 4 MPa below the CPP, preferably no lower than 2 MPa below the CPP). Preferably, the polymerization occurs at a temperature and pressure above the solid-fluid phase transition temperature and pressure of the polymerization system and, preferably above the fluid-fluid phase transition temperature and pressure of the polymerization system.

In an alternate embodiment, the polymerization occurs at a temperature above the solid-fluid phase transition temperature of the polymerization system and a pressure greater than 1 MPa below the cloud point pressure (CPP) of the polymerization system (preferably greater than 0.5 MPa below the CPP, preferably greater than the CCP), and the polymerization occurs: (1) at a temperature below the critical temperature of the polymerization system, or (2) at a pressure below the critical pressure of the polymerization system, preferably the polymerization occurs at a pressure and temperature below the critical point of the polymerization system, most preferably the polymerization occurs: (1) at a temperature below the critical temperature of the polymerization system, and (2) at a pressure below the critical pressure of the polymerization system.

Alternately, the polymerization occurs at a temperature and pressure above the solid-fluid phase transition temperature and pressure of the polymerization system. Alternately, the polymerization occurs at a temperature and pressure above the fluid-fluid phase transition temperature and pressure of the polymerization system. Alternately, the polymerization occurs at a temperature and pressure below the fluid-fluid phase transition temperature and pressure of the polymerization system.

In another embodiment, the polymerization system is preferably a homogeneous, single phase polymerization system, preferably a homogeneous dense fluid polymerization system.

In another embodiment, the reaction temperature is preferably below the critical temperature of the polymerization system. Preferably, the temperature is above the solid-fluid phase transition temperature of the polymer-containing fluid reaction medium at the reactor pressure or at least 5° C. above the solid-fluid phase transition temperature of the polymer-containing fluid reaction medium at the reactor pressure, or at least 10° C. above the solid-fluid phase transformation point of the polymer-containing fluid reaction medium at the reactor pressure. In another embodiment, the temperature is above the cloud point of the single-phase fluid reaction medium at the reactor pressure, or 2° C. or more above the cloud point of the fluid reaction medium at the reactor pressure. In yet another embodiment, the temperature is between 60° C. and 150° C., between 60° C. and 140° C., between 70° C. and 130° C., or between 80° C. and 130° C. In one embodiment, the temperature is above 60° C., 65° C., 70° C., 75° C., 80° C., 85° C., 90° C., 95° C., 100° C., 105° C., or 110° C. In another embodiment, the temperature is below 150° C., 140° C., 130° C., or 120° C. In another embodiment, the cloud point temperature is below the supercritical temperature of the polymerization system or between 70° C. and 150° C.

In another embodiment, the polymerization occurs at a temperature and pressure above the solid-fluid phase transition temperature of the polymerization system, preferably the polymerization occurs at a temperature at least 5° C. higher (preferably at least 10° C. higher, preferably at least 20° C. higher) than the solid-fluid phase transition temperature and at a pressure at least 2 MPa higher (preferably at least 5 MPa higher, preferably at least 10 MPa higher) than the cloud point pressure of the polymerization system. In a preferred embodiment, the polymerization occurs at a pressure above the fluid-fluid phase transition pressure of the polymerization system (preferably at least 2 MPa higher, preferably at least 5 MPa higher, preferably at least 10 MPa higher than the fluid-fluid phase transition pressure). Alternately, the polymerization occurs at a temperature at least 5° C. higher (preferably at least 10° C. higher, preferably at least 20° C. higher) than the solid-fluid phase transition temperature and at a pressure higher than, (preferably at least 2 MPa higher, preferably at least 5 MPa higher, preferably at least 10 MPa higher) than the fluid-fluid phase transition pressure of the polymerization system.

In another embodiment, the polymerization occurs at a temperature above the solid-fluid phase transition temperature of the polymer-containing fluid reaction medium at the reactor pressure, preferably at least 5° C. above the solid-fluid phase transition temperature of the polymer-containing fluid reaction medium at the reactor pressure, or preferably at least 10° C. above the solid-fluid phase transformation point of the polymer-containing fluid reaction medium at the reactor pressure.

In another useful embodiment, the polymerization occurs at a temperature above the cloud point of the single-phase fluid reaction medium at the reactor pressure, more preferably 2° C. or more (preferably 5° C. or more, preferably 10° C. or more, preferably 30° C. or more) above the cloud point of the fluid reaction medium at the reactor pressure. Alternately, in another useful embodiment, the polymerization occurs at a temperature above the cloud point of the polymerization system at the reactor pressure, more preferably 2° C. or more (preferably 5° C. or more, preferably 10° C. or more, preferably 30° C. or more) above the cloud point of the polymerization system.

In another embodiment, the polymerization process temperature is above the solid-fluid phase transition temperature of the polymer-containing fluid polymerization system at the reactor pressure, or at least 2° C. above the solid-fluid phase transition temperature of the polymer-containing fluid polymerization system at the reactor pressure, or at least 5° C. above the solid-fluid phase transition temperature of the polymer-containing fluid polymerization at the reactor pressure, or at least 10° C. above the solid-fluid phase transformation point of the polymer-containing fluid polymerization system at the reactor pressure. In another embodiment, the polymerization process temperature should be above the cloud point of the single-phase fluid polymerization system at the reactor pressure, or 2° C. or more above the cloud point of the fluid polymerization system at the reactor pressure. In still another embodiment, the polymerization process temperature is between 50° C. and 350° C., or between 60° C. and 250° C., or between 70° C. and 250° C., or between 80° C. and 250° C. Exemplary lower polymerization temperature limits are 50° C., or 60° C., or 70° C., or 80° C., or 90° C., or 95° C., or 100° C., or 110° C., or 120° C. Exemplary upper polymerization temperature limits are 350° C., or 250° C., or 240° C., or 230° C., or 220° C., or 210° C., or 200° C.

Polyolefin Products

This invention also relates to compositions of matter produced by the methods described herein.

In a preferred embodiment of the invention, the process described herein produces ethylene copolymers, such as ethylene-alpha-olefin (preferably $C_3$ to $C_{20}$)-cyclic monomer (preferably cyclic diene monomers) copolymers (such as ethylene-propylene-cyclic monomer copolymers, ethylene-hexene-cyclic monomer copolymers, or ethylene-octene-cyclic monomer copolymers having: a Mw/Mn of greater than 1 to 4 (preferably greater than 1 to 3).

In a preferred embodiment of the invention, the process described herein produces ethylene copolymers, such as ethylene-alpha-olefin (preferably $C_3$ to $C_{20}$)-cyclic diene copolymers (such as ethylene-propylene-cyclic diene copolymers, ethylene-hexene-cyclic diene copolymers, or ethylene-octene-cyclic diene copolymers having: a Mw/Mn of greater than 1 to 4 (preferably greater than 1 to 3).

In a preferred embodiment of the invention, the process described herein produces ethylene-propylene-cyclic diene copolymers (such as ethylene-propylene-5-ethylidene-2-norbornene copolymers, ethylene-propylene-norbornadiene copolymers or ethylene-propylene-5-vinyl-2-norbornene copolymers) having: a Mw/Mn of greater than 1 to 4 (preferably greater than 1 to 3).

Non-limiting examples of cyclic olefin monomers (including cyclic dienes, also referred to as cyclic diolefins) useful herein include cyclobutene, cyclopentene, cyclohexene, cycloheptene, cyclooctene, cyclononene, cyclodecene, cyclododecene, norbornene, 4-methylnorbornene, 3-methylcyclopentene, 4-methylcyclopentene, cyclopentadiene, cyclooctadiene, norbornadiene, dicyclopentadiene, 5-ethylidene-2-norbornene, 5-methylidene-2-norbornene, vinylcyclohexene, vinylcyclopentene, vinylcyclobutene, vinylcyclooctene, 5-vinyl-2-norbornene, 7,7-dimethyl-bicyclo[2.2.1]hept-2-ene, tricyclo[4.2.1.0$^{2,5}$]nona-3,7-diene, 5,5-dimethyl-bicyclo[2.2.1]hept-2-ene, 5-ethyl-bicyclo[2.2.1]hept-2-ene, methyl-bicyclo[2.2.1]hept-2-ene, 2,3,3a,4,7,7a-hexahydro-4,7-methano-1H-indene, 5-ethenylidene-bicyclo[2.2.1]hept-2-ene, 5,6-dimethyl-bicyclo[2.2.1]hept-2-ene, 5-ethynyl-bicyclo[2.2.1]hept-2-ene, 7-oxanorbornene, 7-oxanorbornadiene, and substituted derivatives thereof, and preferably norbornene, norbornadiene, dicyclopentadiene, 5-ethylidene-2-norbornene, 5-methylidene-2-norbornene, vinylcyclohexene, and 5-vinyl-2-norbornene, most preferably 5-ethylidene-2-norbornene.

In some embodiments, the cyclic olefin monomer is preferably a cyclic diene monomer such as cyclopentadiene, cyclooctadiene, norbornadiene, dicyclopentadiene, 5-ethylidene-2-norbornene, 5-methylidene-2-norbornene, vinylcyclohexene, vinylcyclopentene, vinylcyclobutene, vinylcyclooctene, 5-vinyl-2-norbornene, tricyclo[4.2.1.0$^{2,5}$]nona-3,7-diene, preferably norbornadiene, dicyclopentadiene, 5-ethylidene-2-norbornene, and 5-methylidene-2-norbornene, most preferably 5-ethylidene-2-norbornene.

Generally, the process of this invention produces olefin polymers, preferably ethylene-$C_3$ to $C_{12}$ alpha olefin-cyclic diene copolymers. In a preferred embodiment, the polymers produced herein are copolymers of ethylene preferably having from: 1) 1 to 90 mole % (alternately from 1 to 80 mole %, alternately from 1 to 60 mole %, alternately from 5 to to 50 mole %, alternately from 10 to 45 mole %, alternately from 20 to 40 mole %) of one or more $C_3$ to $C_{12}$ olefin comonomer (preferably $C_3$ to $C_{12}$ alpha-olefin, preferably propylene, butene, hexene, octene, decene, dodecene, preferably propylene, butene, hexene, octene, most preferably propylene); 2) from 0 to 25 mole % (alternately from 0.5 to 20 mole %, alternately from 1 to 15 mole %, alternately from 3 to 12 mole %, preferably from 3 to 10 mole %) of one or more of cyclic diene comonomers (preferably norbornadiene, dicyclopentadiene, 5-ethylidene-2-norbornene, and or 5-vinyl-2-norbornene, most preferably 5-ethylidene-2-norbornene); and 3) the balance preferably made up of by ethylene.

In a preferred embodiment, the monomer is ethylene preferably having from 1 to 90 mole % (alternately from 1 to 80 mole %, alternately from 1 to 60 mole %, alternately from 5 to 50 mole %, alternately from 10 to 45 mole %, alternately from 20 to 40 mole %) and the comonomer is propylene, preferably from 1 to 60 mole % propylene, alternately 5 to 55 mole %, alternatively 10 to 45 mole %, alternatively 20 to 40 mol %, and the cyclic olefin monomer is a cyclic diene, preferably from 1 to 40 mol %, alternatively from 1 to 25 mole %, alternately 1 to 20 mole %, alternatively 1 to 10 mole %, alternatively 1 to 5 mole %, alternatively 1 to 3 mole % of one or more of norbornadiene, 5-ethylidene-2-norbornene, dicyclopentadiene, and/or 5-vinyl-2-norbornene, most preferably 5-ethylidene-2-norbornene.

In a preferred embodiment, the monomer is ethylene preferably present at from 20 to 70 mole % (alternately from 30 to 60 mole %, alternately from 35 to 55 mole %, alternately from 40 to 50 mole %, the comonomer is propylene, preferably present at from 30 to 70 mole % propylene, alternately 40 to 60 mole %, alternatively 45 to 55 mole %, alternatively 50 to 60 mol %, and the cyclic olefin monomer is a cyclic diene, preferably present at from 1 to 20 mol %, alternatively from 1 to 15 mole %, alternately 1 to 10 mole %, alternatively 1 to 5 mole %, alternatively 1 to 3 mole %, alternatively 1 to 2 mole % of one or more of norbornadiene, 5-ethylidene-2-norbornene, dicyclopentadiene, and/or 5-vinyl-2-norbornene, most preferably 5-ethylidene-2-norbornene.

In a preferred embodiment, the ethylene-propylene-cyclic monomer copolymer contains greater than 50% vinyl end-group unsaturation, alternately greater than 60% vinyl end-group unsaturation, alternately greater than 70% vinyl end-group unsaturation, alternately alternately greater than 80% vinyl end-group unsaturation, alternately greater than 90% vinyl end-group unsaturation, alternately greater than 95% vinyl end-group unsaturation.

Typically, the polymers produced herein have an Mw of 3,000 to 5,000,000 g/mol (alternatively 5,000 to 3,000,000 g/mol, alternatively 10,000 to 2,500,000 g/mol, alternatively 50,000 to 2,00,000 g/mol, alternatively 75,000 to 1,000,000 g/mol, alternatively 100,000 to 500,000 g/mol, alternatively 100,000 to 250,000 g/mol), and/or an Mw/Mn of greater than 1 to 40 (alternately 1.2 to 20, alternately 1.3 to 10, alternately 1.4 to 5, 1.5 to 4, alternately 1.5 to 3).

In a preferred embodiment the polymer produced herein has a unimodal or multimodal molecular weight distribution (MWD=Mw/Mn) as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

In a preferred embodiment the copolymers produced herein have a composition distribution breadth index (CDBI) of 50% or more, preferably 60% or more, preferably 70% or more. CDBI is a measure of the composition distribution of monomer within the polymer chains and is measured by the procedure described in WO 93/03093, published Feb. 18, 1993, specifically columns 7 and 8 as well as in Wild et al, J. Poly. Sci., Poly. Phys. Ed., Vol. 20, p. 441 (1982) and U.S. Pat. No. 5,008,204, including that fractions having a weight average molecular weight (Mw) below 10,000 g/mol are ignored when determining CDBI.

The polymers produced herein typically have at least 50% allyl chain ends or 3-alkyl chain ends (preferably at least 60%, at least 70%, at least 80%, at least 90%, at least 95%, at least 98%, or at least 99% allyl chain ends and/or 3-alkyl chain ends).

An allyl chain end is represented by $CH_2CH—CH_2$—, as shown in the formula:

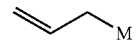

where M represents the polymer chain. "Allylic vinyl group," "allyl chain end," "vinyl chain end," "vinyl termination," "allylic vinyl group," and "vinyl terminated" are used interchangeably in the following description. The number of allyl chain ends, vinylidene chain ends, vinylene chain ends, and other unsaturated chain ends is determined using $^1$H NMR at 120° C. using deuterated tetrachloroethane as the solvent on an at least 250 MHz NMR spectrometer, and in selected cases, confirmed by $^{13}$C NMR. Resconi has reported proton and carbon assignments (neat perdeuterated tetrachloroethane used for proton spectra, while a 50:50 mixture of normal and perdeuterated tetrachloroethane was used for carbon spectra; all spectra were recorded at 100° C. on a BRUKER spectrometer operating at 500 MHz for proton and 125 MHz for carbon) for vinyl terminated oligomers in J. American Chemical Soc., 114, 1992, pp. 1025-1032 that are useful herein. Allyl chain ends are reported as a molar percentage of the total number of moles of unsaturated groups (that is, the sum of allyl chain ends, vinylidene chain ends, vinylene chain ends, and the like).

A 3-alkyl chain end (where the alkyl is a $C_1$ to $C_{38}$ alkyl), also referred to as a "3-alkyl vinyl end group" or a "3-alkyl vinyl termination", is represented by the formula:

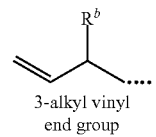

3-alkyl vinyl end group where "••••" represents the polyolefin chain and $R^b$ is a $C_1$ to $C_{38}$ alkyl group, or a $C_1$ to $C_{20}$ alkyl group, such as methyl, ethyl, propyl, butyl, pentyl, hexyl, heptyl, octyl, nonyl, decyl, undecyl, dodecyl, and the like. The amount of 3-alkyl chain ends is determined using $^1$H NMR as set out below. The chemical shift regions for the olefin types are defined to be between the following spectral regions.

| Unsaturation Type | Region (ppm) | Number of hydrogens per structure |
|---|---|---|
| Vinyl | 4.98-5.13 | 2 |
| Vinylidene (VYD) | 4.69-4.88 | 2 |
| Vinylene | 5.31-5.55 | 2 |
| Trisubstituted | 5.11-5.30 | 1 |

In a preferred embodiment of the invention, the polymer produced herein is an ethylene-propylene-cyclic monomer copolymer having from 0.1 to 50 mol % comonomer) and having: 1) at least 50% allyl chain ends; and 2) an Mw of 5000 g/mol or more.

In a preferred embodiment of the invention, the polymer produced herein is a has a branching index ($g'_{vis}$) of 0.95 or less, preferably 0.90 or less, preferably 0.87 or less, preferably 0.85 or less, preferably 0.80 or less, preferably 0.75 or less, as determined by GPC, as described in the Examples section below.

The polymers prepared herein may be functionalized by reacting a heteroatom containing group with the polymer with or without a catalyst. Examples include catalytic hydrosilylation, ozonolysis, hydroformylation, or hydroamination, sulfonation, halogenation, hydrohalogenation, hydroboration, epoxidation, or Diels-Alder reactions with polar dienes, Friedel-Crafts reactions with polar aromatics, maleation with activators such as free radical generators (e.g., peroxides). The functionalized polymers can be used in oil additives, as anti-fogging or wetting additives, adhesion promoters and many other applications. Preferred uses include additives for lubricants and or fuels. Preferred heteroatom containing groups include, amines, aldehydes, alcohols, acids, anhydrides, sulphonates, particularly succinic acid, maleic acid and maleic anhydride.

Other uses of the functionalized polymers include as plasticizers, surfactants for soaps, detergents, fabric softeners, antistatics, etc. Preferred heteroatom containing groups include, amines, aldehydes, alcohols, acids, anhydrides, and sulphonates, particularly succinic acid, maleic acid and maleic anhydride.

In some embodiments the polymers produced herein are functionalized as described in U.S. Pat. No. 6,022,929; A. Toyota, T. Tsutsui, and N. Kashiwa, Polymer Bulletin 48, 213-219, 2002; and J. Am. Chem. Soc., 1990, 112, 7433-7434.

Blends

In another embodiment, the polymer produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

Any of the foregoing polymers, including blends thereof, may be used in a variety of end-use applications. Such applications include, for example, mono- or multi-layer blown, extruded, and/or shrink films. These films may be formed by any number of well known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or a double bubble process and may occur before or after the individual layers are brought together. Typically the films are oriented in the Machine Direction (MD) at a ratio of up to 15, preferably between 5 and 7, and in the Transverse Direction (TD) at a ratio of up to 15, preferably 7 to 9. However, in another embodiment the film is oriented to the same extent in both the MD and TD directions.

The films may vary in thickness depending on the intended application; however, films of a thickness from 1 to 50 µm are usually suitable. Films intended for packaging are usually from 10 to 50 µm thick. The thickness of the sealing layer is typically 0.2 to 50 µm. There may be a sealing layer on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment, one or both of the surface layers is modified by corona treatment.

Molded Products

The polymers described herein (preferably ethylene-propylene-cyclic monomer polymers) and blends thereof may also be used to prepare molded products in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art.

Further, the polymers described herein (preferably ethylene-propylene-cyclic monomer polymers) may be shaped into desirable end use articles by any suitable means known in the art. Thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof are typically used methods.

Thermoforming is a process of forming at least one pliable plastic sheet into a desired shape. Typically, an extrudate film of the composition of this invention (and any other layers or materials) is placed on a shuttle rack to hold it during heating. The shuttle rack indexes into the oven which pre-heats the film before forming. Once the film is heated, the shuttle rack indexes back to the forming tool. The film is then vacuumed onto the forming tool to hold it in place and the forming tool is closed. The tool stays closed to cool the film and the tool is then opened. The shaped laminate is then removed from the tool. The thermoforming is accomplished by vacuum, positive air pressure, plug-assisted vacuum forming, or combinations and variations of these, once the sheet of material reaches thermoforming temperatures, typically of from 140° C. to 185° C. or higher. A pre-stretched bubble step is used, especially on large parts, to improve material distribution.

Blow molding is another suitable forming means for use with the compositions of this invention, which includes injection blow molding, multi-layer blow molding, extrusion blow molding, and stretch blow molding, and is especially suitable for substantially closed or hollow objects, such as, for example, gas tanks and other fluid containers. Blow molding is described in more detail in, for example, CONCISE ENCYCLOPEDIA OF POLYMER SCIENCE AND ENGINEERING, pp. 90-92 (Jacqueline I. Kroschwitz, ed., John Wiley & Sons 1990).

Likewise, molded articles may be fabricated by injecting molten polymer into a mold that shapes and solidifies the molten polymer into desirable geometry and thickness of molded articles. Sheets may be made either by extruding a substantially flat profile from a die, onto a chill roll, or alternatively by calendaring. Sheets are generally considered to have a thickness of from 10 mils to 100 mils (254 µm to 2540 µm), although any given sheet may be substantially thicker.

Any of the foregoing polymers, including compounds thereof, may be used in a variety of end-use applications. Such applications include, for example, mono- or multi-layer blown, extruded, and/or shrink films. These films may be formed by any number of well known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film.

The present polymer compositions can further be used in a variety of applications such as barrier layers, weather seals, coolant hoses, roofing membranes, wire and cable insulation, dynamically vulcanized alloys, power transmission belts, engine mounts, thermoplastic blends, elastic fibers, and the like.

The present polymer compositions can further be used in automotive parts, consumer goods, industrial goods, construction materials, and packaging materials, including, but are not limited to, an extruded article, such as an automotive weatherseal, a non-automotive weatherseal, a building profile; a molded article, such as a seal, a gasket; a hose, such as air hose, heat hose, garden hose, industry hose; a roof sheet; a film; or a cable jacket.

EXPERIMENTAL

Test Methods for Large Scale Polymerizations
Gel Permeation Chromatography

Mw, Mn, Mz, number of carbon atoms and $g'_{vis}$ are determined by using a High Temperature Size Exclusion Chromatograph (either from Waters Corporation or Polymer Laboratories), equipped with three in-line detectors, a differential refractive index detector (DRI), a light scattering (LS) detector, and a viscometer. Experimental details, including detector calibration, are described in: T. Sun, P. Brant, R. R. Chance, and W. W. Graessley, Macromolecules, Volume 34, Number 19, 6812-6820, (2001) and references therein. Three Polymer Laboratories PLgel 10 mm Mixed-B LS columns are used. The nominal flow rate is 0.5 cm$^3$/min, and the nominal injection volume is 300 µL. The various transfer lines, columns and differential refractometer (the DRI detector) are contained in an oven maintained at 145° C. Solvent for the experiment is prepared by dissolving 6 grams of butylated hydroxy toluene as an antioxidant in 4 liters of Aldrich reagent grade 1, 2, 4 trichlorobenzene (TCB). The TCB mixture is then filtered through a 0.7 µm glass pre-filter and subsequently through a 0.1 µm Teflon filter. The TCB is then degassed with an online degasser before entering the Size Exclusion Chromatograph. Polymer solutions are prepared by placing dry polymer in a glass container, adding the desired amount of TCB, then heating the mixture at 160° C. with continuous agitation for about 2 hours. All quantities are measured gravimetrically. The TCB densities used to express the polymer concentration in mass/volume units are 1.463 g/ml at room temperature and 1.324 g/ml at 145° C. The injection concentration is from 0.75 to 2.0 mg/ml, with lower concentrations being used for higher molecular weight samples. Prior to running each sample the DRI detector and the injector are purged. Flow rate in the apparatus is then increased to 0.5 ml/minute, and the DRI is allowed to stabilize for 8 to 9 hours before injecting the first sample. The LS laser is turned on 1 to 1.5 hours before running the samples. The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system. The refractive index, n=1.500 for TCB at 145° C. and λ=690 nm. For purposes of this invention and the claims thereto (dn/dc)=0.104 for propylene polymers, 0.098 for butene polymers and 0.1 otherwise. Units on parameters throughout this description of the SEC method are such that concentration is expressed in g/cm³, molecular weight is expressed in g/mole, and intrinsic viscosity is expressed in dL/g.

The LS detector is a Wyatt Technology High Temperature mini-DAWN. The molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{MP(\theta)} + 2A_2 c$$

Here, $\Delta R(\theta)$ is the measured excess Rayleigh scattering intensity at scattering angle θ, c is the polymer concentration determined from the DRI analysis, $A_2$ is the second viral coefficient [for purposes of this invention, $A_2$=0.0006 for propylene polymers, 0.0015 for butene polymers and 0.001 otherwise], (dn/dc)=0.104 for propylene polymers, 0.098 for butene polymers and 0.1 otherwise, P(θ) is the form factor for a monodisperse random coil, and $K_o$ is the optical constant for the system:

$$K_o = \frac{4\pi^2 n^2 (dn/dc)^2}{\lambda^4 N_A}$$

where NA is Avogadro's number, and (dn/dc) is the refractive index increment for the system. The refractive index, n=1.500 for TCB at 145° C. and λ=690 nm.

A high temperature Viscotek Corporation viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, $\eta_S$, for the solution flowing through the viscometer is calculated from their outputs. The intrinsic viscosity, [η], at each point in the chromatogram is calculated from the following equation:

$$\eta_S = c[\eta] + 0.3(c[\eta])^2$$

where c is concentration and was determined from the DRI output.

The branching index ($g'_{vis}$) is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromatographic slices, i, between the integration limits. The branching index $g'_{vis}$ is defined as:

$$g'vis = \frac{[\eta]_{avg}}{kM_v^\alpha}$$

where, for purpose of this invention and claims thereto, α=0.695 and k=0.000579 for linear ethylene polymers, α=0.705 k=0.000262 for linear propylene polymers, and α=0.695 and k=0.000181 for linear butene polymers. Mv is the viscosity-average molecular weight based on molecular weights determined by LS analysis.

Mooney Large viscosity (ML) and Mooney Relaxation Area (MLRA): ML and MLRA are measured using a Mooney viscometer according to ASTM D-1646, modified as detailed in the following description. A square sample is placed on either side of the rotor. The cavity is filled by pneumatically lowering the upper platen. The upper and lower platens are electrically heated and controlled at 125° C. The torque to turn the rotor at 2 rpm is measured by a torque transducer. Mooney viscometer is operated at an average shear rate of 2 s⁻¹. The sample is pre-heated for 1 minute after the platens are closed. The motor is then started and the torque is recorded for a period of 4 minutes. The results are reported as ML (1+4) 125° C., where M is the Mooney viscosity number, L denotes large rotor, 1 is the pre-heat time in minutes, 4 is the sample run time in minutes after the motor starts, and 125° C. is the test temperature.

The torque limit of the Mooney viscometer is about 100 Mooney units. Mooney viscosity values greater than about 100 Mooney unit cannot generally be measured under these conditions. In this event, a non-standard rotor design is employed with a change in Mooney scale that allows the same instrumentation on the Mooney viscometer to be used for more viscous polymers. This rotor that is both smaller in diameter and thinner than the standard Mooney Large (ML) rotor is termed MST—Mooney Small Thin. Typically when the MST rotor is employed, the test is also run at different time and temperature. The pre-heat time is changed from the standard 1 minute to 5 minutes and the test is run at 200° C. instead of the standard 125° C. Thus, the value will be reported as MST (5+4), 200° C. Note that the run time of 4 minutes at the end which the Mooney reading is taken remains the same as the standard conditions. According to EP 1 519 967, one MST point is approximately 5 ML points when MST is measured at (5+4@200° C.) and ML is measured at (1+4@125° C.). The MST rotor should be prepared as follows:

1. The rotor should have a diameter of 30.48+/−0.03 mm and a thickness of 2.8+/−0.03 mm (tops of serrations) and a shaft of 11 mm or less in diameter.
2. The rotor should have a serrated face and edge, with square grooves of 0.8 mm width and depth of 0.25-0.38 mm cut on 1.6 mm centers. The serrations will consist of two sets of grooves at right angles to each other (form a square crosshatch).
3. The rotor shall be positioned in the center of the die cavity such that the centerline of the rotor disk coincides with the centerline of the die cavity to within a tolerance of +/−0.25 mm. A spacer or a shim may be used to raise the shaft to the midpoint.
4. The wear point (cone shaped protuberance located at the center of the top face of the rotor) shall be machined off flat with the face of the rotor.

The MLRA data is obtained from the Mooney viscosity measurement when the rubber relaxes after the rotor is stopped. The MLRA is the integrated area under the Mooney torque-relaxation time curve from 1 to 100 seconds. The MLRA is a measure of chain relaxation in molten polymer and can be regarded as a stored energy term which suggests that, after the removal of an applied strain, the longer or branched polymer chains can store more energy and require longer time to relax. Therefore, the MLRA value of a bimodal rubber (the presence of a discrete polymeric fraction with very high molecular weight and distinct composition) or a long chain branched rubber are larger than a broad or a narrow molecular weight rubber when compared at the same Mooney viscosity values.

Mooney Relaxation Area is dependent on the Mooney viscosity of the polymer, and increases with increasing Mooney viscosity. In order to remove the dependence on polymer Mooney Viscosity, a corrected MLRA (cMLRA) parameter is used, where the MLRA of the polymer is normalized to a reference of 80 Mooney viscosity. The formula for cMLRA is provided below:

$$cMLRA = MLRA\left(\frac{80}{ML}\right)^{1.44}$$

where MLRA and ML are the Mooney Relaxation Area and Mooney viscosity of the polymer sample measured at 125° C.

Alternatively, the ratio MLRA/ML may be used to remove the dependence on polymer Mooney Viscosity. This ratio has the dimension of time. A higher MLRA/ML number signifies a higher degree of melt elasticity. Long chain branching will slow down the relaxation of the polymer chain, hence increasing the value of MLRA/ML.

Ethylene content is determined using FTIR according the ASTM D3900 and is not corrected for diene content. ENB content is determined using FTIR according to ASTM D6047.

EXAMPLES

Starting Materials

All manipulations with air and moisture sensitive compounds were performed either in an atmosphere of thoroughly purified argon using standard Schlenk techniques or in a controlled atmosphere glove box (Vacuum Atmospheres Co.). Tetrahydrofuran (THF, Merck=Merck KGaA, Darmstadt, Germany) and diethyl ether (ether, Merck) for synthesis were purified by distillation over LiAlH$_4$, and stored over sodium benzophenone ketyl under an inert atmosphere; prior to use, the solvents were distilled from the benzophenone ketyl. Hydrocarbon solvents such as toluene (Merck), and hexanes (Merck) were typically distilled over CaH$_2$, and were stored over Na/K alloy under an inert atmosphere; prior to use, the solvents were distilled from the Na/K alloy. Methylene chloride (and CCl$_2$D$_2$ for NMR measurements) was distilled and stored over CaH$_2$ under an inert atmosphere; prior to use, the solvent was distilled from the CaH$_2$. Celite (Aldrich) was dried in a vacuum oven at 180° C. p-Toluenesulfonic acid (TsOH, Aldrich), 2.5 M "BuLi in hexanes (Chemetall GmbH), MeMgBr in ether (Aldrich), and HfCl$_4$ (Strem), Na$_2$SO$_4$ (Akzo Nobel), methanol (Merck), sodium lump (Merck), ZnCl$_2$ (Merck), 3-chloropropanoyl chloride (Acros), potassium hydroxide (Merck), AlCl$_3$ (Merck), 12 M HCl (diluted as needed; Reachim, Moscow, Russia), 96% H$_2$SO$_4$ (diluted as needed; Reachim), anhydrous K$_2$CO$_3$ (Merck), CuCN (Merck), hydrazine hydrate (Merck), silica gel 60 (40-63 um; Merck), NaHCO$_3$ (Merck), ethylene glycol (Merck), Na$_2$CO$_3$ (Aldrich), and CDCl$_3$ (Deutero GmbH) were used as received.

1,1-Dichlorosilolane was obtained as described in [West, R. J. Am. Chem. Soc., 1954, 76, 6015-6017] and [Denmark, S. E.; Griedel, B. D.; Coe, D. M.; Schnute, M. E., J. Am. Chem. Soc., 1994, 116, 7026-7043].

Analytical and semi-preparative liquid chromatography was performed using a Waters Delta 600 HPLC system including a 996 Photodiode Array Detector, Nova-Pack C18 or HR Silica (60A, 6 μm, 3.9 and 19×300 mm) and Symmetry C18 (5 μm, 4.6×250 mm) columns. MPLC (Medium Pressure Liquid Chromatography, pressure 5-15 bars) was performed using MPLC glass columns and fittings (Ace Glass), a PD5130 pump drive equipped with a J1 gear-well pump head (Heidolph), a 996 Photodiode Array Detector and a Fraction Collector II (Waters Corp.). $^1$H and $^{13}$C spectra were recorded with a Brucker Avance-400 spectrometer. Chemical shifts for $^1$H and $^{13}$C were measured relative to tetramethylsilane (TMS). $^1$H NMR spectral assignments were made on the basis of double resonance and Nuclear Overhauser Effect (NOE) experiments. CHN microanalyses were done using a CHN—O-Rapid analyzer (Heraecus Ltd., Banau, Germany).

Synthesis of rac-cyclotetramethylenesilylene-bis[4,8-dimethyl-1,2,3-trihydro-s-indacen-5-yl]hafnium dimethyl (compound 19)

4,7-Dimethylindane

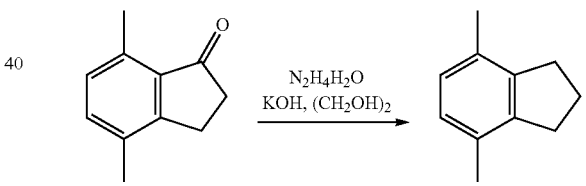

A mixture of 124 g (2.21 mol) of KOH, 91.4 g (570.5 mmol) of 4,7-dimethylindan-1-one, 102 ml of hydrazine hydrate, and 1100 ml of ethylene glycol was heated under reflux for 5 h. Then, the reflux condenser was replaced by a Claisen distillation head with condenser, and a mixture of water, NH$_2$NH$_2$, the product and ethylene glycol was distilled until the vapor temperature reached 195° C. The obtained distillate was diluted with 1000 ml of water, and crude product was extracted with 3×250 ml of dichloromethane. The combined organic extract was washed by 1 M HCl, dried over anhydrous K$_2$CO$_3$, and then passed through a short pad of silica gel 60 (40-63 um). The obtained filtrate was evaporated to dryness to give a slightly yellowish liquid. This liquid was distilled in vacuum to give 68.1 g (82%) of 4,7-dimethylindane as a colorless liquid, b.p. 88-90° C./10 mm Hg.

Anal. calc. for C$_{11}$H$_{14}$: C, 90.35; H, 9.65. Found: C, 90.31; H, 9.48. $^1$H NMR (CDCl$_3$): δ 6.86 (s, 2H), 2.82 (t, J=7.6 Hz, 4H), 2.21 (s, 6H), 2.05 (quint, J=7.6 Hz, 2H). $^{13}$C{$^1$H} NMR (CDCl$_3$): δ 142.53, 130.84, 126.99, 31.62, 24.17, 18.86.

4,8-Dimethyl-3,5,6,7-tetrahydro-s-indacen-1(2H)-one

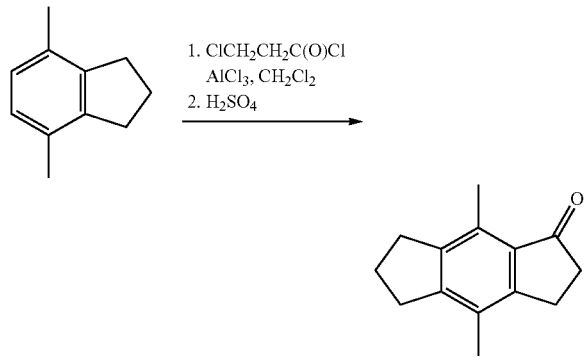

To a stirred suspension of 133.4 g (1.0 mol) of AlCl$_3$ in 600 ml of dichloromethane a solution of 111.5 g (878 mmol) of 3-chloropropanoyl chloride and 121.8 g (833 mmol) of 4,7-dimethylindane in 100 ml of dichloromethane was added dropwise over 3 h at room temperature. This mixture was stirred additionally overnight at room temperature and then poured on 1000 g of crushed ice. The organic layer was separated, and the aqueous layer was extracted with 3×100 ml of dichloromethane. The combined organic extract was washed by aqueous K$_2$CO$_3$, dried over K$_2$CO$_3$, passed through a short pad of silica gel 60 (40-63 um), and then evaporated to dryness to give dark oily liquid. This liquid was added to 1000 ml of sulfuric acid and then stirred for 1 h at room temperature. The resulting dark solution was heated for 30 min to 90° C. and then stirred for one hour at the same temperature. After cooling to room temperature the reaction mixture was poured on 2000 g of crushed ice and 3000 ml of cold water. Then, 1 liter of dichloromethane was added. The organic layer was separated, and the aqueous layer was extracted with dichloromethane (100 ml per 900 ml of aqueous phase). The combined organic extract was washed by water, then by aqueous K$_2$CO$_3$, dried over K$_2$CO$_3$ and passed through a short layer of silica gel 60 (40-63 um). The elute was evaporated to ca. 500 ml, and the title product was isolated by flash-chromatography on 1000 ml of silica gel 60 (40-63 um; eluent: dichloromethane). This procedure gave 90.3 g (54%) of 4,8-dimethyl-3,5,6,7-tetrahydro-s-indacen-1(2H)-one as a slightly yellowish solid.

Anal. calc. for C$_{14}$H$_{16}$O: C, 83.96; H, 8.05. Found: C, 84.30; H, 8.27. $^1$H NMR (CDCl$_3$): δ 2.94-2.82 (m, 6H), 2.70-2.62 (m, 2H), 2.53 (s, 3H), 2.19 (s, 3H), 2.12 (quin, J=7.5 Hz, 2H). $^{13}$C{$^1$H} NMR (CDCl$_3$): δ 208.15, 153.92, 149.93, 143.01, 132.88, 131.04, 127.84, 37.40, 31.98, 30.72, 24.57, 23.70, 14.33, 14.30.

4,8-Dimethyl-1,2,3,5-tetrahydro-s-indacene

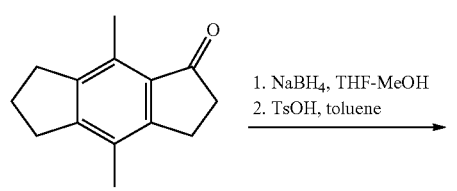

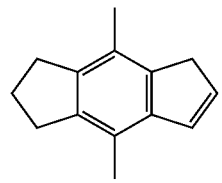

To a solution of 90.3 g (450.7 mmol) of 4,8-dimethyl-3,5,6,7-tetrahydro-s-indacen-1(2H)-one in 900 ml of THF cooled to 5° C. 25.6 g (677 mmol) of NaBH$_4$ was added. Further on, 250 ml of methanol was added dropwise to this mixture by vigorous stirring for ca. 5 h at 5° C. The resulting mixture was evaporated to dryness, and the residue was partitioned between 1000 ml of dichloromethane and 700 ml of 1 M HCl. The organic layer was separated, the aqueous layer was additionally extracted with 200 ml of dichloromethane. The combined organic extract was evaporated to dryness to give a white solid. To a solution of this solid in 1500 ml of toluene 0.5 g of TsOH was added, this mixture was refluxed with Dean-Stark head for 15 min and then cooled to room temperature using water bath. The resulting solution was washed by 10% aqueous Na$_2$CO$_3$, the organic layer was separated, the aqueous layer was extracted with 2×150 ml of dichloromethane. The combined organic extract was dried over K$_2$CO$_3$ and then passed through a short layer of silica gel 60 (40-63 um). The silica gel layer was additionally washed by 100 ml of dichloromethane. The combined organic elute was evaporated to dryness to give a brownish solid mass. The product was isolated by flash-chromatography on 1000 ml of silica gel 60 (40-63 um; eluent: hot hexane) followed by recrystallization from n-hexane. This procedure gave 65.4 g (79%) of 4,8-dimethyl-1,2,3,5-tetrahydro-s-indacene as a white crystalline solid.

Anal. calc. for C$_{14}$H$_{16}$: C, 91.25; H, 8.75. Found: C, 91.11; H, 8.62. $^1$H NMR (CDCl$_3$): δ 6.97 (dt, J=5.5 Hz, J=1.9 Hz, 1H), 6.48 (dt, J=5.5 Hz, J=1.9 Hz, 1H), 3.27 (s, 2H), 2.93-2.85 (m, 4H), 2.33 (s, 3H), 2.25 (s, 3H), 2.11 (quin, J=7.5 Hz, 2H). $^{13}$C{$^1$H} NMR (CDCl$_3$): δ 141.97, 141.27, 140.91, 139.73, 132.40, 130.48, 126.11, 123.36, 37.93, 31.54, 31.46, 25.00, 15.66, 15.42.

rac-cyclotetramethylenesilylene-bis[4, 8-dimethyl-1,2,3-trihydro-s-indacen-5-yl]hafnium dichloride, otherwise named rac-1,1-Silolanediyl-bis(4,8-dimethyl-1,5,6,7-tetrahydro-s-indacen-1-yl)hafnium dichloride

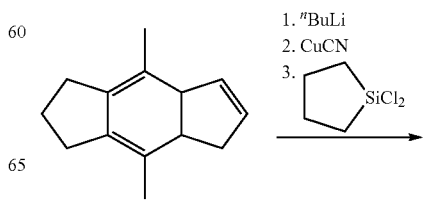

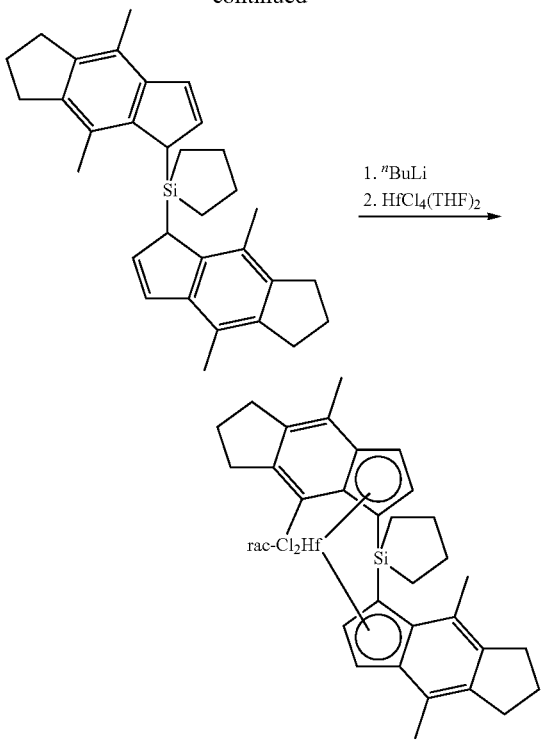

To a solution of 13.8 g (75 mmol) of 4,8-dimethyl-1,2,3,5-tetrahydro-s-indacene in 420 ml of ether 30 ml (75 mmol) of 2.5 M $^n$BuLi in hexanes was added in one portion at −50° C. This mixture was stirred for 3 h at room temperature, then the resulting light-yellow solution with a large amount of heavy white precipitate was cooled to −50° C., and 200 mg of CuCN was added. The resulting mixture was stirred for 15 min at −25° C., and then 5.82 g (37.52 mmol) of 1,1-dichlorosilolane was added in one portion. The formed mixture was stirred overnight at ambient temperature, then it was filtered through glass frit (G4), and the obtained slightly yellowish solution was further used without an additional purification. To the above-prepared solution of 37.5 mmol (assuming almost quantitative yield) of 1,1-bis (4,8-dimethyl-1,5,6,7-tetrahydro-s-indacen-1-yl)silolane cooled to −50° C. 30.0 ml (75 mmol) of 2.5 M $^n$BuLi in hexanes was added in one portion. This mixture was stirred overnight at room temperature. The resulting almost colorless solution with a lot of white precipitate was cooled to −50° C., and 12.0 g (37.5 mmol) of HfCl$_4$ was added. The reaction mixture was stirred for 24 h resulting in light red solution with a large amount of yellow precipitate. The obtained mixture was evaporated to dryness, and the residue was heated with 250 ml of toluene. This suspension was filtered while hot through glass frit (G4). The filtrate was evaporated to 120 ml and then heated to dissolve the formed precipitate. Yellow powder precipitated overnight at room temperature was collected and dried in vacuum. This procedure gave 8.10 g of pure rac-1,1-silolanediyl-bis(4,8-dimethyl-1,5,6,7-tetrahydro-s-indacen-1-yl)hafnium dichloride. The mother liquor was evaporated to ca. 60 ml. Yellow powder precipitated from this solution overnight at room temperature was collected and dried in vacuum. This procedure gave 3.10 g of rac-1,1-silolanediyl-bis(4,8-dimethyl-1,5,6,7-tetrahydro-s-indacen-1-yl)hafnium dichloride. Again, the mother liquor was evaporated to ca. 25 ml, and 60 ml of n-hexane was added. After stirring for 30 min the precipitated orange solid was filtered off and then dried in vacuum. This procedure gave 5.00 g of a ca. 3:1 mixture of rac-/meso-complexes. Thus, the total yield of rac- and meso-complexes isolated in this synthesis was 16.2 g (62%).

Anal. calc. for C$_{32}$H$_{36}$Cl$_2$HfSi: C, 55.05; H, 5.20. Found: C, 55.24; H, 5.39. $^1$H NMR (CDCl$_3$): δ 6.84 (d, J=3.5 Hz, 2H), 6.00 (d, J=3.5 Hz, 2H), 3.07-2.79 (m, 8H), 2.44 (s, 6H), 2.25 (s, 6H), 2.23-2.15 (m, 2H), 2.12-1.93 (m, 4H), 1.92-1.73 (m, 4H), 1.67-1.57 (m, 2H). $^{13}$C{$^1$H} NMR (CDCl$_3$): δ 143.56, 142.42, 131.44, 127.03, 125.65, 124.73, 117.02, 117.01, 89.60, 31.80, 31.01, 26.78, 25.17, 19.50, 17.44, 15.78.

rac-cyclotetramethylenesilylene-bis[4, 8-dimethyl-1,2,3-trihydro-s-indacen-5-yl]hafnium dimethyl, otherwise named rac-1,1-Silolanediyl-bis(4,8-dimethyl-1,5,6,7-tetrahydro-s-indacen-1-yl)hafnium dimethyl (Compound 19)

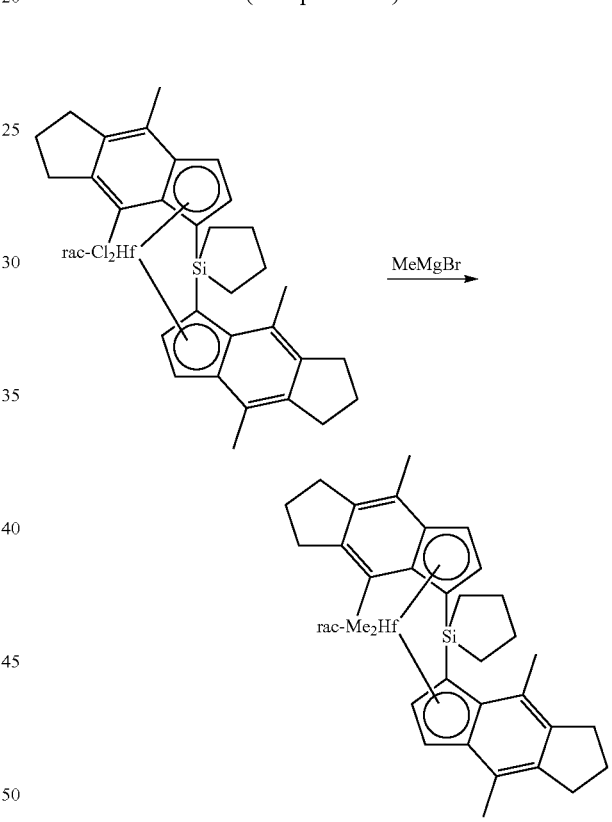

To a solution of 8.10 g (11.6 mmol) of rac-1,1-silolanediyl-bis(4,8-dimethyl-1,5,6,7-tetrahydro-s-indacen-1-yl)hafnium dichloride in a mixture of 140 ml of toluene and 40 ml of ether 24.0 ml (50.6 mmol) of 2.11 M MeMgBr in ether was added. The resulting mixture was refluxed for 30 min, then evaporated to ca. 50 ml, heated and filtered while hot through glass frit (G3) to remove insoluble magnesium salts. The filter cake was additionally washed with 2×15 ml of toluene. The combined filtrate was evaporated to ca. 400 ml, heated and again filtered while hot through glass frit (G3). Light yellow crystals precipitated from the filtrate overnight at room temperature were collected and dried in vacuum. This procedure gave 5.60 g (74%) of pure rac-1,1-silolanediyl-bis(4,8-dimethyl-1,5,6,7-tetrahydro-s-indacen-1-yl)hafnium dimethyl.

Anal. calc. for $C_{34}H_{42}HfSi$: C, 62.13; H, 6.44. Found: C, 62.19; H, 6.60. $^1$H NMR (CDCl$_3$): δ 6.83 (d, J=3.4 Hz, 2H), 5.75 (d, J=3.4 Hz, 2H), 3.01-2.88 (m, 4H), 2.88-2.73 (m, 4H), 2.35 (s, 6H), 2.29 (s, 6H), 2.18-2.07 (m, 2H), 2.02 (quin, J=7.4 Hz, 4H), 1.81-1.67 (m, 2H), 1.67-1.54 (m, 2H), 1.53-1.44 (m, 2H), −1.79 (s, 6H). $^{13}$C{$^1$H} NMR (CDCl$_3$): δ 140.87, 139.99, 129.14, 126.21, 125.30, 124.97, 117.81, 110.49, 84.94, 38.73, 31.74, 30.99, 26.86, 25.40, 19.38, 17.47, 16.03.

List of Catalysts

Compounds used in the following polymerization examples include the following wherein the associated number is the compound number, also referred to the CAT ID in polymerization example tables.

rac-cyclopentamethylenesilylene-bis[4,7-dimethylinden-1-yl]hafniumdimethyl (12)

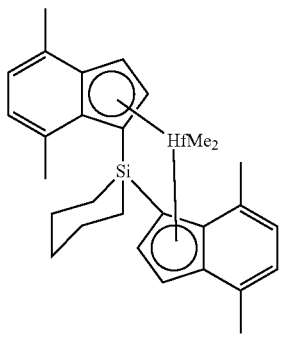

rac-cyclotetramethylenesilyene-bis[4,7-dimethylinden-1-yl]hafnium dimethyl (14)

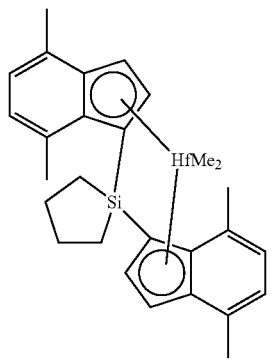

rac-cyclotetramethylenesilyene-bis[4,8-dimethyl-1,2,3-trihydro-s-indacen-5-yl]hafnium dimethyl (19)

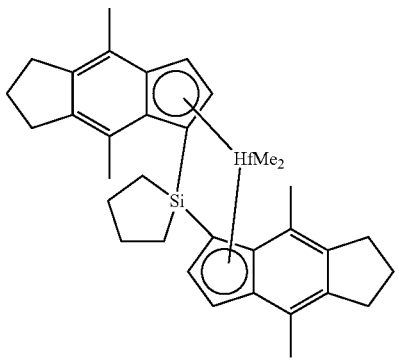

rac-cyclotetramethylenesilyene-bis(2,4,7-trimethylinden-1-yl)hafnium dimethyl (2)

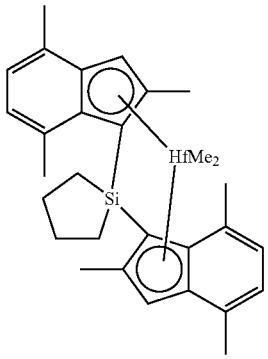

rac-cyclotetramethylenesilylene-bis[4,6,8-trimethyl-1,2,3-trihydro-s-indacen-5-yl]hafnium dimethyl (16)

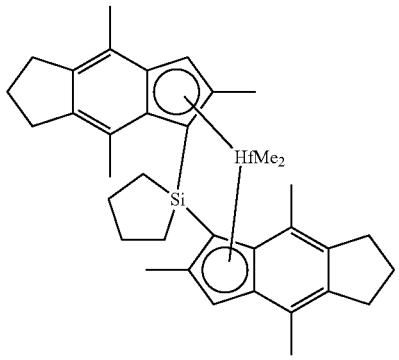

rac-cyclotetramethylenesilylene-bis(2-methyl-4-isopropylinden-1-yl)hafnium dichloride(8)

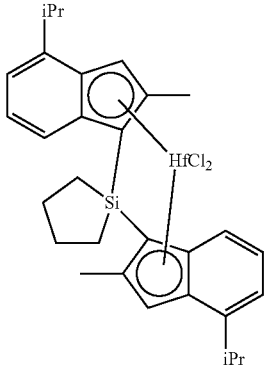

-continued rac-cyclotrimethylenesilylene-bis
(2,4,7-trimethylinden-1-yl)hafnium
dichloride (17)

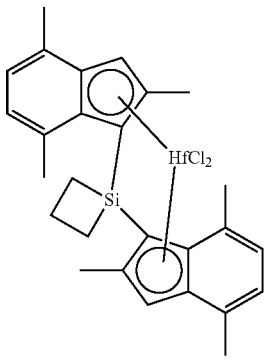

rac-cyclotetramethylenesilylene-bis
(2-ethyl-4-cyclopropylinden-1-yl)
hafnium dichloride (5)

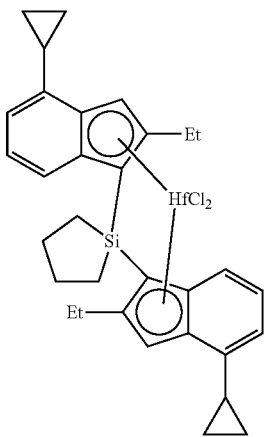

rac-cyclotrimethylenesilylene-bis(2-
ethyl-4-cyclopropylinden-1-yl)
hafnium dichloride (6)

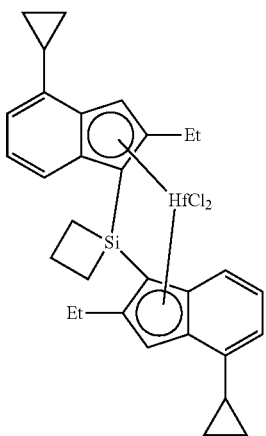

-continued rac-dimethlenesilylene-bis(2-methyl-
4-phenylinden-1-yl)zirconium
dimethyl (20)

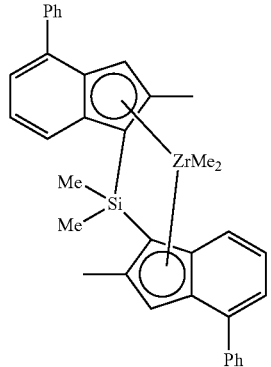

Compounds 2, 5, 6, 8, 12, 14, 16, and 17 were prepared as described in U.S. Ser. No. 14/325,449, filed Jul. 8, 2014 and U.S. Ser. No. 61/847,442, filed Jul. 17, 2013.

Comparative compounds used in the following polymerization examples include compounds 2, 5, 6, 8, 16, 17 and 20 all of which have 2 alkyl substituents on the indenyl rings.

Small Scale Polymerization Examples

Solutions of the pre-catalysts (Compounds 2, 5, 6, 8, 12, 14, 16, 17, 19, and 20) were made using toluene (ExxonMobil Chemical-anhydrous, stored under $N_2$) (98%). Pre-catalyst solutions were typically 0.5 mmol/L. When noted, some pre-catalysts were pre-alkylated using triisobutyl aluminum (TiBAl, neat, AkzoNobel); prealkylation was performed by first dissolving the pre-catalyst in the appropriate amount of toluene, and then adding 20 equivalents of TiBAl such that the final pre-catalyst solution was 0.5 mmol precatalyst/L and 10 mmol TiBAl/L.

Solvents, polymerization grade toluene and/or isohexanes were supplied by ExxonMobil Chemical Co. and are purified by passing through a series of columns: two 500 cc Oxyclear cylinders in series from Labclear (Oakland, Calif.), followed by two 500 cc columns in series packed with dried 3 Å mole sieves (8-12 mesh; Aldrich Chemical Company), and two 500 cc columns in series packed with dried 5 Å mole sieves (8-12 mesh; Aldrich Chemical Company).

5-ethylidene2-norbornene (ENB, Aldrich) was sparged by nitrogen, filtered through basic alumina (Aldrich Chemical Company, Brockman Basic 1) and stored under an inert atmosphere of dry nitrogen.

Polymerization grade ethylene was used and further purified by passing it through a series of columns: 500 cc Oxyclear cylinder from Labclear (Oakland, Calif.) followed by a 500 cc column packed with dried 3 Å mole sieves (8-12 mesh; Aldrich Chemical Company), and a 500 cc column packed with dried 5 Å mole sieves (8-12 mesh; Aldrich Chemical Company).

Activation of the pre-catalysts was by dimethylanilinium tetrakisperfluorophenylborate (Boulder Scientific and Albemarle Corp). Dimethylanilinium tetrakisperfluorophenylborate was typically used as a 5 mmol/L solution in toluene.

For polymerization runs using dimethylanilinium tetrakisperfluorophenylborate tri-n-octylaluminum (TnOAl, Neat, AkzoNobel) was also used as a scavenger prior to introduction of the activator and pre-catalyst into the reactor. TnOAl was typically used as a 5 mmol/L solution in toluene.

Reactor Description and Preparation:

Polymerizations were conducted in an inert atmosphere ($N_2$) drybox using autoclaves equipped with an external heater for temperature control, glass inserts (internal volume of reactor=23.5 mL), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25° C. for 5 hours.

Ethylene/ENB Copolymerization:

The reactor was prepared as described above, and then purged with ethylene. For dimethylanilinium tetrakisperfluorophenylborate activated runs, isohexane, ENB (50 µL) and scavenger (TnOAl, 0.075 mol) were added via syringe at room temperature and atmospheric pressure. The reactor was then brought to process temperature (100° C.) and charged with ethylene to process pressure (100 psig=790.8 kPa) while stirring at 800 RPM. The activator solution (0.088 umol of activator), followed by the pre-catalyst solution (0.080 umol of pre-catalyst), was injected via syringe to the reactor at process conditions. Ethylene was allowed to enter (through the use of computer controlled solenoid valves) the autoclaves during polymerization to maintain reactor gauge pressure (+/−2 psig). Reactor temperature was monitored and typically maintained within +/−1° C. Polymerizations were halted by addition of approximately 50 psi $CO_2$/Ar (50/50) gas mixture to the autoclave for approximately 30 seconds. The polymerizations were quenched after a predetermined cumulative amount of ethylene had been added (maximum quench value of 20 psi) or for a maximum of 30 minutes polymerization time (maximum quench time). Afterwards, the reactors were cooled and vented. While still under an inert atmosphere, the polymers were stabilized with the addition of a 50 uL solution of a Irganox 1076 and Irgafos 168 in toluene (prepared by dissolving 0.5 g of each antioxidant in a total of 10 ml toluene). Polymers were isolated after the solvent was removed in-vacuo. Yields reported include total weight of polymer, antioxidant and residual catalyst. Catalyst activity is reported as kilograms of polymer per mmol transition metal compound per hour of reaction time (kg/mmol*hr). Small scale ethylene/ENB copolymerization runs are summarized in Table 1.

Polymer Characterization

For analytical testing, polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 165° C. in a shaker oven for approximately 3 hours. The typical concentration of polymer in solution was between 0.1 to 0.9 mg/mL with a BHT concentration of 1.25 mg BHT/mL of TCB. Samples were cooled to 135° C. for testing.

High temperature size exclusion chromatography was performed using an automated "Rapid GPC" system as described in U.S. Pat. Nos. 6,491,816; 6,491,823; 6,475,391; 6,461,515; 6,436,292; 6,406,632; 6,175,409; 6,454,947; 6,260,407; and 6,294,388; each of which is incorporated herein by reference. Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with dual wavelength infrared detector and calibrated using polystyrene standards (Polymer Laboratories: Polystyrene Calibration Kit S-M-10: Mp (peak Mw) between 580 and 3,039,000). Samples (250 µL of a polymer solution in TCB were injected into the system) were run at an eluent flow rate of 2.0 mL/minute (135° C. sample temperatures, 165° C. oven/columns) using three Polymer Laboratories: PLgel 10 µm Mixed-B 300×7.5 mm columns in series. No column spreading corrections were employed. Numerical analyses were performed using Epoch® software available from Symyx Technologies or Automation Studio software available from Freeslate. The molecular weights obtained are relative to linear polystyrene standards. Molecular weight data is reported in Tables 1 under the headings Mn, Mw and PDI as defined above. Differential Scanning Calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minute and then cooled at a rate of 50° C./minute. Melting points were collected during the heating period. The results are reported in the Table 1, $T_m$ (° C.).

Wt % ENB was calculated using the $T_m$ and the following equation:

$$\text{Wt \% ENB} = (128.36 - T_m)/2.57$$

where $T_m$ is the melting point (° C.) of the polymer as measured by DSC as described directly above. The equation was developed from a correlation between wt % ENB measured via $^1H$ NMR and DSC measurements of ethylene-ENB copolymers ranging from 0.8 to 26.6 wt % ENB as determined by $^1H$ NMR. ENB content of the polymers used in the calibration was determined as follows: The $^1H$ solution NMR was performed on a 5 mm probe at a field of at least 500 MHz in tetrachloroethane-d2 solvent (or a 80:20 v/v ortho-dichlorobenzene and $C_6D_6$ mixture) at 120° C. with a flip angle of 30°, 15 s delay and 512 transients. Signals were integrated and the ENB weight percent was reported.

For calculation of ENB:
$I_{major}$=Integral of major ENB species from 5.2-5.4 ppm
$I_{minor}$=Integral of minor ENB species from 4.6-5.12 ppm
$I_{eth}$=(Integral of —$CH_2$— from 0-3 ppm)
total=(ENB+E)
total wt=(ENB*120+E*14)

| Peak Assignments | Intensity of species | MOLE % | WEIGHT % |
|---|---|---|---|
| ENB | ENB = $I_{major}$ + $I_{minor}$ | ENB * 100/total | ENB * 120 * 100/total wt |
| Ethylene (E) | E = ($I_{eth}$ − 11 * ENB)/2 | E * 100/total | E * 14 * 100/total wt |

Polymerization results are collected in Table 1 below. "Ex#" stands for example number. Examples starting with a "C" are comparative examples. "Cat ID" identifies the pre-catalyst/compound used in the experiment. Corresponding numbers identifying the pre-catalyst are located above. An asterisk next to the Cat ID number indicates that the pre-catalyst was pre-alkylated with 20 equivalents of TiBAl. "Yield" is polymer yield, and is not corrected for catalyst residue or antioxidant content. "Quench time (s)" is the actual duration of the polymerization run in seconds. If a polymerization quench time is less than the maximum time set (30 min), then the polymerization ran until the set maximum value of ethylene uptake was reached. ENB conversion (%) was calculated from the grams of ENB in the polymer times 100, divided by the gram of ENB added to the reactor. The grams of ENB in the polymer was calculated from the calculated ENB wt % in the polymer times the polymer yield in grams and dividing by 100. The density used for ENB was 0.893 g/ml.

liquid phase. The reactors were operated liquid full. Solvents and monomers were first purified over beds of alumina and molecular sieves. Purification columns were regenerated periodically whenever there was evidence of lower activity of polymerization. All liquid feeds were pumped into the

TABLE 1

Ethylene-ENB copolymerization examples

| Ex# | Cat ID | quench time (s) | yield (g) | Activity (kg P/mmol cat · hr) | Mn (g/mol) | Mw (g/mol) | Mz (g/mol) | PDI (Mw/Mn) | Tm (° C.) | Calc. ENB (wt %) | Calc. ENB conversion (%) |
|---|---|---|---|---|---|---|---|---|---|---|---|
| 1 | 12 | 33 | 0.099 | 135 | 151,093 | 433,041 | 1,240,264 | 2.87 | 89.3 | 15.2 | 33.7 |
| 2 | 12 | 26 | 0.099 | 171 | 138,242 | 423,640 | 1,305,830 | 3.06 | 97.8 | 11.9 | 26.4 |
| 3 | 12 | 40 | 0.097 | 109 | 209,242 | 569,323 | 1,502,105 | 2.72 | 91.1 | 14.5 | 31.4 |
| 4 | 12 | 27 | 0.097 | 162 | 132,155 | 390,119 | 1,092,133 | 2.95 | 94.2 | 13.3 | 28.8 |
| 5 | 14 | 31 | 0.099 | 144 | 150,089 | 443,455 | 1,326,847 | 2.95 | 91.5 | 14.3 | 31.8 |
| 6 | 14 | 37 | 0.100 | 122 | 172,848 | 471,933 | 1,323,577 | 2.73 | 92.6 | 13.9 | 31.1 |
| 7 | 14 | 32 | 0.098 | 138 | 171,601 | 472,515 | 1,255,718 | 2.75 | 92.9 | 13.8 | 30.2 |
| 8 | 14 | 44 | 0.085 | 87 | 262,688 | 566,053 | 1,381,921 | 2.15 | 88.0 | 15.7 | 29.9 |
| 9 | 14 | 37 | 0.116 | 141 | 287,772 | 1,021,515 | 3,829,558 | 3.55 | 85.9 | 16.5 | 42.9 |
| 10 | 14 | 66 | 0.118 | 81 | 206,429 | 1,083,504 | 4,634,392 | 5.25 | 91.3 | 14.4 | 38.2 |
| 11 | 14 | 33 | 0.107 | 145 | 220,122 | 529,304 | 1,365,911 | 2.40 | 88.8 | 15.4 | 36.7 |
| 12 | 14 | 34 | 0.114 | 151 | 173,399 | 455,141 | 1,097,208 | 2.62 | 85.4 | 16.7 | 42.6 |
| 13 | 19 | 30 | 0.121 | 181 | 377,161 | 1,318,764 | 4,604,667 | 3.50 | 74.3 | 21.0 | 56.8 |
| 14 | 19 | 42 | 0.121 | 130 | 333,882 | 780,611 | 1,635,358 | 2.34 | 71.0 | 22.3 | 60.4 |
| 15 | 19 | 40 | 0.119 | 134 | 311,937 | 694,525 | 1,428,476 | 2.23 | 71.7 | 22.0 | 58.6 |
| C1 | 2 | 70 | 0.095 | 61 | 347,076 | 1,082,173 | 3,347,662 | 3.12 | 121.6 | 2.6 | 5.6 |
| C2 | 2 | 319 | 0.057 | 8 | 804,276 | 1,481,642 | 3,809,758 | 1.84 | 119.3 | 3.5 | 4.5 |
| C3 | 2 | 82 | 0.103 | 57 | 377,623 | 738,988 | 1,518,285 | 1.96 | 121.7 | 2.6 | 6.0 |
| C4 | 2 | 45 | 0.087 | 87 | 200,702 | 478,129 | 1,158,721 | 2.38 | 122.5 | 2.3 | 4.4 |
| C5 | 2 | 58 | 0.088 | 68 | 209,575 | 490,504 | 1,255,389 | 2.34 | 122.0 | 2.5 | 4.9 |
| C6 | 2 | 36 | 0.082 | 102 | 215,637 | 460,694 | 1,044,499 | 2.14 | 122.5 | 2.3 | 4.2 |
| C7 | 2 | 38 | 0.081 | 96 | 201,649 | 488,385 | 1,233,020 | 2.42 | 122.6 | 2.2 | 4.1 |
| C8 | 16 | 173 | 0.047 | 12 | 667,181 | 1,090,619 | 1,992,120 | 1.63 | 119.0 | 3.6 | 3.8 |
| C9 | 16 | 51 | 0.073 | 64 | 479,435 | 932,874 | 1,910,821 | 1.95 | 119.8 | 3.3 | 5.4 |
| C10 | 16 | 47 | 0.076 | 73 | 333,096 | 750,027 | 1,700,794 | 2.25 | 121.6 | 2.6 | 4.5 |
| C11 | 16 | 44 | 0.073 | 75 | 375,304 | 750,308 | 1,495,978 | 2.00 | 121.2 | 2.8 | 4.6 |
| C12 | 8* | 1800 | 0.024 | 0.60 | 199,868 | 392,603 | 911,025 | 1.96 | 115.7 | 4.9 | 2.6 |
| C13 | 8* | 1801 | 0.020 | 0.50 | 205,613 | 366,867 | 774,935 | 1.78 | 114.9 | 5.2 | 2.3 |
| C14 | 8* | 1801 | 0.022 | 0.55 | 220,320 | 406,282 | 986,649 | 1.84 | 115.9 | 4.8 | 2.4 |
| C15 | 8* | 1701 | 0.029 | 0.77 | 221,594 | 400,677 | 852,111 | 1.81 | 116.2 | 4.7 | 3.1 |
| C16 | 17* | 1801 | 0.012 | 0.30 | 142,432 | 310,087 | 825,692 | 2.18 | 122.7 | 2.2 | 0.6 |
| C17 | 17* | 1801 | 0.010 | 0.25 | | | | | | | |
| C18 | 17* | 1802 | 0.015 | 0.38 | 187,746 | 386,390 | 1,108,036 | 2.06 | 123.4 | 1.9 | 0.6 |
| C19 | 17* | 1800 | 0.006 | 0.15 | | | | | | | |
| C20 | 5* | 1464 | 0.022 | 0.68 | 272,598 | 507,927 | 1,205,764 | 1.86 | 119.3 | 3.5 | 1.7 |
| C21 | 5* | 1801 | 0.027 | 0.68 | 277,425 | 523,298 | 1,219,566 | 1.89 | 119.2 | 3.6 | 2.2 |
| C22 | 5* | 1800 | 0.032 | 0.80 | 296,734 | 544,121 | 1,263,615 | 1.83 | 121.0 | 2.9 | 2.1 |
| C23 | 5* | 1546 | 0.033 | 0.96 | 268,623 | 537,167 | 1,344,362 | 2.00 | 121.3 | 2.7 | 2.0 |
| C24 | 6* | 1801 | 0.005 | 0.12 | | | | | | | |
| C25 | 6* | 1800 | 0.010 | 0.25 | | | | | | | |
| C26 | 6* | 1800 | 0.012 | 0.30 | 218,868 | 490,841 | 1,909,729 | 2.24 | 117.7 | 4.1 | 1.1 |
| C27 | 6* | 1800 | 0.009 | 0.22 | | | | | | | |
| C28 | 20 | 49 | 0.071 | 65 | 201,733 | 405,763 | 1,049,372 | 2.01 | 122.8 | 2.2 | 3.4 |
| C29 | 20 | 41 | 0.075 | 81 | 188,520 | 383,215 | 876,596 | 2.03 | 123.0 | 2.1 | 3.5 |
| C30 | 20 | 44 | 0.072 | 74 | 194,966 | 403,391 | 961,063 | 2.07 | 124.0 | 1.7 | 2.7 |
| C31 | 20 | 44 | 0.071 | 72 | 175,538 | 396,669 | 1,048,595 | 2.26 | 123.5 | 1.9 | 3.0 |

For all runs, 0.34 ml toluene and 4.6 ml isohexane was used.

The above data shows that the inventive catalysts are capable of incorporating greater amounts of ENB versus the comparative catalysts given the same polymerization conditions. Additionally, ENB conversion for the inventive catalysts ranged from 26-60% whereas conversion for the comparative catalysts ranged from 0.6 to 5.4%.

Large Scale Polymerization Examples

The ethylene copolymers in Examples L1 to L8 were made in a continuous stirred-tank reactor system with a 1 liter Autoclave reactor. The reactors were equipped with a stirrer, a water cooling/steam heating element with a temperature controller, and a pressure controller. The reactor was maintained at a pressure in excess of the bubbling point pressure of the reactant mixture to keep the reactants in the liquid phase. The reactors were operated liquid full. Solvents and monomers were first purified over beds of alumina and molecular sieves. Purification columns were regenerated periodically whenever there was evidence of lower activity of polymerization. All liquid feeds were pumped into the reactors by a Pulsa feed pump. All liquid flow rates were controlled using Brooks mass flow controller. Ethylene was delivered as a gas solubilized in the chilled solvent/monomer mixture. The purified solvents and monomers were then chilled to about −7° C. by passing through a chiller before being fed into the reactors through a manifold. Solvent and monomers were mixed in the manifold and fed into reactor through a single tube. Similarly, activated catalyst solution was fed using an ISCO syringe pump. Catalyst and monomer contacts took place in the reactor.

The reactors were first prepared by continuously $N_2$ purging at a maximum allowed temperature, then pumping isohexane and scavenger solution through the reactor system for at least one hour. Monomers and catalyst solutions were then fed into the reactor for polymerization. Once the activity was established and the system reached equilibrium, the reactor was lined out by continuing operation of the system under the established condition for a time period of at least five times of mean residence time prior to sample collection. The polymer produced in the reactor exited through a back pressure control valve that reduced the pressure to atmospheric. This caused the unconverted monomers in the solution to flash into a vapor phase which was vented from the top of a liquid vapor separator. The liquid phase, comprising mainly polymer and solvent, was collected for polymer recovery. The collected samples were first air-dried in a hood to evaporate most of the solvent, and then dried in a vacuum oven at a temperature of about 90° C. for about 12 hours. The vacuum oven dried samples were weighed to obtain yields. All the reactions were carried out at a gauge pressure of about 2.7 MPa.

Catalysts used were rac-cyclotetramethylenesilylene-bis[4,7-dimethylinden-1-yl]hafnium dimethyl (14), rac-cyclotetramethylenesilylene-bis[4,8-dimethyl-1,2,3-trihydro-s-indacen-5-yl]hafnium dimethyl (19) and comparative rac-cyclotetramethylenesilylene-bis(2,4,7-trimethylinden-1-yl) hafnium dimethyl (2) and the activator used was N,N-dimethylanilinium tetrakis(heptafluoro-2-naphthyl)borate (available from Albemarle Corporation). The metallocene catalysts were preactivated with the activator at a molar ratio of 1:1 in 900 ml of toluene. All catalyst solutions were kept in an inert atmosphere. Tri-n-octylaluminum (TNOAL) solution (available from Sigma Aldrich, Milwaukee, Wis.) was further diluted in isohexane and used as a scavenger. Scavenger feed rate was adjusted to maximize the catalyst efficiency. The catalyst feed rate can be adjusted to achieve the yield and monomer conversion. The detailed process condition and some analytical results are summarized in Table 2.

TABLE 2

Ethylene-propylene - ENB copolymerizations

| | Example # | | | |
|---|---|---|---|---|
| | L1 | L2 | L3 | L4 |
| Polymerization temperature (° C.) | 120 | 120 | 120 | 120 |
| Ethylene feed rate (g/min) | 6.79 | 6.79 | 6.79 | 6.79 |
| Propylene feed rate (g/min) | 6 | 6 | 6 | 6 |
| ENB feed rate (g/min) | 1.33 | 1.33 | 1.33 | 1.78 |
| Isohexane feed rate (g/min) | 82.7 | 82.7 | 82.7 | 82.7 |
| Catalyst ID | 14 | 14 | 19 | 19 |
| Catalyst feed rate (mol/min) | 5.538E−07 | 4.500E−07 | 1.980E−07 | 3.043E−07 |
| Conversion (%) | 80.9% | 83.6% | 48.9% | 59.4% |
| ML (mu) | * | * | 40.1 | 34 |
| MLRA (mu-sec) | | | 210.2 | 192.1 |
| MST (mu) | | | 9.1 | 8.5 |
| MST RA (mst-sec) | | | 90.9 | 87.7 |
| Mn_DRI (g/mol) | | | | 57,021 |
| Mw_DRI (g/mol) | | | | 135,413 |
| Mz_DRI (g/mol) | | | | 262,617 |
| Mw/Mn | | | | 2.37 |
| Mn_LS (g/mol) | | | | 67,985 |
| Mw_LS (g/mol) | | | | 142,558 |
| Mz_LS (g/mol) | | | | 302,033 |
| g'vis | | | | 0.872 |
| Ethylene content (wt %) | | | 73.87 | 70.78 |
| ENB (wt %) | * | * | 6.76 | 8.48 |
| ENB conversion (%) | | | 35.4 | 36.1 |

| | Example # | | | |
|---|---|---|---|---|
| | L5 | L6 | L7 | Comp. L8 |
| Polymerization temperature (° C.) | 120 | 120 | 120 | 120 |
| Ethylene feed rate (g/min) | 6.79 | 6.79 | 6.79 | 6.79 |
| Propylene feed rate (g/min) | 6 | 6 | 6 | 6 |
| ENB feed rate (g/min) | 1.78 | 1.78 | 1.78 | 1.33 |
| Isohexane feed rate (g/min) | 82.7 | 82.7 | 82.7 | 82.7 |
| Catalyst | 19 | 19 | 19 | 2 |
| Catalyst feed rate (mol/min) | 2.282E−07 | 1.521E−07 | 1.065E−07 | 3.300E−07 |
| Conversion (%) | 53.9% | 54.0% | 49.6% | 41.5% |
| ML (mu) | 58.8 | 69.8 | 74.6 | 2.4 |
| MLRA (mu-sec) | 444.2 | 662.7 | 847 | |
| MST (mu) | 15.3 | 19.1 | 21 | |
| MST RA (mst-sec) | 180.3 | 268.1 | 330.8 | |
| Mn_DRI (g/mol) | 64,997 | 80,492 | 80,708 | |
| Mw_DRI (g/mol) | 178,087 | 224,061 | 218,561 | |
| Mz_DRI (g/mol) | 354,917 | 498,295 | 444,450 | |
| Mw/Mn | 2.74 | 2.78 | 2.71 | |
| Mn_LS (g/mol) | 83,186 | 102,132 | 93,956 | |
| Mw_LS (g/mol) | 194,223 | 238,884 | 251,675 | |
| Mz_LS (g/mol) | 412,152 | 473,557 | 583,426 | |
| g'vis | 0.873 | 0.835 | 0.84 | |

TABLE 2-continued

| Ethylene-propylene - ENB copolymerizations | | | | |
|---|---|---|---|---|
| Ethylene content (wt %) | 73.3 | 73.8 | 74.58 | 73.6 |
| ENB (wt %) | 8.36 | 8.21 | 8.01 | 1.27 |
| ENB conversion (%) | 32.4 | 31.9 | 28.6 | 5.6 |

* Polymer produced was of lower molecular weight and sticky.

All documents described herein are incorporated by reference herein, including any priority documents and/or testing procedures to the extent they are not inconsistent with this text, provided however that any priority document not named in the initially filed application or filing documents is not incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

The invention claimed is:

1. A process for producing copolymers comprising ethylene, a $C_3$ to $C_{12}$ alpha olefin, and a cyclic olefin monomer, said process comprising contacting ethylene, a $C_3$ to $C_{12}$ alpha-olefin, and a cyclic olefin monomer, with activator and a metallocene catalyst compound represented by the formula (I):

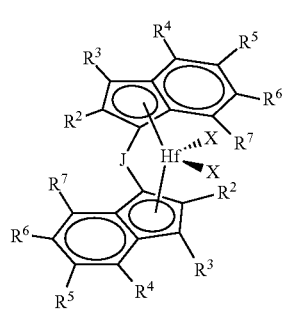

(I)

where each $R^2$ and $R^3$ is hydrogen; each $R^4$ is independently a $C_1$-$C_{10}$ alkyl; each $R^5$, $R^6$ and $R^7$ is independently hydrogen, $C_1$-$C_{50}$ substituted or unsubstituted hydrocarbyl, or $C_1$-$C_{50}$ substituted or unsubstituted halocarbyl; and $R^4$ and $R^5$, $R^5$ and $R^6$ and/or $R^6$ and $R^7$ are optionally bonded together to form a ring structure; J is a bridging group represented by the formula $R^a{}_2J$, where J is C or Si, and each $R^a$ is, independently, $C_1$ to $C_{20}$ substituted or unsubstituted hydrocarbyl, and the two $R^a$ form a cyclic structure incorporating J and the cyclic structure is optionally a saturated or partially saturated cyclic or fused ring system; and each X is a univalent anionic ligand, or two Xs are joined and bound to the metal atom to form a metallocycle ring, or two Xs are joined to form a chelating ligand, a diene ligand, or an alkylidene ligand.

2. The process of claim 1 wherein the conversion of cyclic olefin monomer is greater than 6% based on the weight of cyclic monomer used in the process and the weight of cyclic monomer incorporated into the polymer.

3. The process of claim 1 wherein $R^4$ and $R^7$ are, independently, a $C_1$ to $C_{10}$ alkyl, and $R^2$, $R^3$, $R^5$ and $R^6$ are hydrogen.

4. The process of claim 1 wherein $R^4$ and $R^7$ are, independently, selected from the group consisting of methyl, ethyl, propyl, butyl, pentyl, heptyl, hexyl, octyl, nonyl, decyl and isomers thereof.

5. The process of claim 1 wherein $R^4$ and $R^7$ are, independently, a $C_1$ to $C_{10}$ alkyl.

6. The process of claim 1 wherein each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's optionally form a part of a fused ring or a ring system).

7. The process of claim 1 wherein J is represented by the formula:

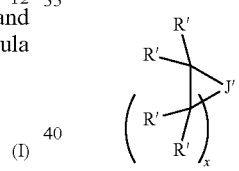

wherein J' is a carbon or silicon atom, x is 1, 2, 3, or 4, and each R' is, independently, hydrogen or $C_1$-$C_{10}$ hydrocarbyl.

8. The process of claim 1 wherein J is cyclopentamethylenesilylene, cyclotetramethylenesilylene, cyclotrimethylenesilylene.

9. The process of claim 1 wherein the metallocene catalyst compound is selected from the group consisting of:
cyclotetramethylenesilylene-bis(4,7-dimethylinden-1-yl) hafnium dimethyl,
cyclopentamethylenesilylene-bis(4,7-dimethylinden-1-yl)hafnium dimethyl,
cyclotrimethylenesilylene-bis(4,7-dimethylinden-1-yl) hafnium dimethyl,
cyclotetramethylenesilylene-bis(4,7-dimethylinden-1-yl) hafnium dichloride,
cyclopentamethylenesilylene-bis(4,7-dimethylinden-1-yl)hafnium dichloride,
cyclotrimethylenesilylene-bis(4,7-dimethylinden-1-yl) hafnium dichloride,
cyclotetramethylenesilylene-bis(4,7-diethylinden-1-yl) hafnium dimethyl,
cyclopentamethylenesilylene-bis(4,7-diethylinden-1-yl) hafnium dimethyl, cyclotrimethylenesilylene-bis(4,7-diethylinden-1-yl)hafnium dimethyl,
cyclotetramethylenesilylene-bis(4,7-diethylinden-1-yl) hafnium dichloride,
cyclopentamethylenesilylene-bis(4,7-diethylinden-1-yl) hafnium dichloride,
cyclotrimethylenesilylene-bis(4,7-diethylinden-1-yl)hafnium dichloride,
cyclotetramethylenesilylene-bis(4,8-dimethyl-1,2,3-trihydro-s-indacen-5-yl)hafnium dimethyl,
cyclopentamethylenesilylene-bis(4,8-dimethyl-1,2,3-trihydro-s-indacen-5-yl)hafnium dimethyl,
cyclotrimethylenesilylene-bis(4,8-dimethyl-1,2,3-trihydro-s-indacen-5-yl)hafnium dimethyl,
cyclotetramethylenesilylene-bis(4,8-dimethyl-1,2,3-trihydro-s-indacen-5-yl)hafnium dichloride,
cyclopentamethylenesilylene-bis(4,8-dimethyl-1,2,3-trihydro-s-indacen-5-yl)hafnium dichloride,
cyclotrimethylenesilylene-bis(4,8-dimethyl-1,2,3-trihydro-s-indacen-5-yl)hafnium dichloride; and any compound where the dimethyl in any of the compounds listed above is replaced with diethyl, dipropyl, diphenyl, dibenzyl, difloride, dibromide, or diiodide.

10. The process of claim 1 wherein the activator comprises alumoxane.

11. The process of claim 1 wherein alumoxane is present at a molar ratio of aluminum to catalyst compound transition metal of 100:1 or more.

12. The process of claim 1 wherein the activator comprises a non-coordinating anion activator.

13. The process of claim 1 wherein activator is represented by the formula:

$$(Z)_d^+(A^{d-})$$

wherein Z is (L-H) or a reducible Lewis Acid, L is an neutral Lewis base; H is hydrogen; (L-H)$^+$ is a Bronsted acid; A$^{d-}$ is a non-coordinating anion having the charge d−; and d is an integer from 1 to 3.

14. The process of claim 1 wherein activator is represented by the formula:

$$(Z)_d^+(A^{d-})$$

wherein A$^{d-}$ is a non-coordinating anion having the charge d−; d is an integer from 1 to 3, and Z is a reducible Lewis acid represented by the formula: (Ar$_3$C$^+$), where Ar is aryl or aryl substituted with a heteroatom, a C$_1$ to C$_{40}$ hydrocarbyl, or a substituted C$_1$ to C$_{40}$ hydrocarbyl.

15. The process of claim 1 wherein the activator is one or more of: N,N-dimethylanilinium tetrakis(pentafluorophenyl)borate, triphenylcarbenium tetrakis(pentafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, [4-t-butyl-PhNMe$_2$H] [(C$_6$F$_3$(C$_6$F$_5$)$_2$)$_4$B], trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate, triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium) tetrakis(3,5-bis(trifluoromethyl)phenyl)borate, di-(i-propyl)ammonium tetrakis(pentafluorophenyl)borate, dicyclohexylammonium tetrakis(pentafluorophenyl)borate, tri(o-tolyl)phosphonium tetrakis (pentafluorophenyl)borate, tri(2,6-dimethylphenyl) phosphonium tetrakis(pentafluorophenyl)borate, triphenylcarbenium tetrakis(perfluorophenyl)borate, 1-(4-(tris(pentafluorophenyl)borate)-2,3,5,6-tetrafluorophenyl) pyrrolidinium, tetrakis(pentafluorophenyl)borate, 4-(tris (pentafluorophenyl)borate)-2,3,5,6-tetrafluoropyridine, and triphenylcarbenium tetrakis(3,5-bis(trifluoromethyl)phenyl) borate).

16. The process of claim 1 wherein the catalyst system is supported.

17. The process of claim 1 wherein the catalyst system is supported on silica.

18. The process of claim 1 wherein the catalyst system comprises two catalyst compounds at least one of which is represented by the formula (I).

19. The process of claim 1 wherein the process occurs at a temperature of from about 0° C. to about 300° C., at a pressure in the range of from about 0.35 MPa to about 20 MPa, and at a time up to 300 minutes.

20. The process of claim 1 further comprising obtaining copolymer having at least 50% allyl chain ends.

21. The process of claim 1 wherein the copolymer comprises from 1 to 80 mol % ethylene, from 0 to 60 mol % propylene and from 1 to 40 mol % cyclic monomer.

22. The process of claim 1 wherein the copolymer comprises from 1 to 80 mol % ethylene, from 0 to 60 mol % propylene and from 1 to 40 mol % vinylnorbornene, norbornadiene, and or ethylidene norbornene.

23. The process of claim 1 wherein the copolymer has having at least 50% allyl chain ends and comprises from 1 to 80 mol % ethylene, from 0 to 60 mol % propylene and from 1 to 40 mol % vinylnorbornene, norbornadiene, and or ethylidene norbornene.

24. The process of claim 1 wherein $R^4$ and $R^7$ are, independently, a $C_1$ to $C_{10}$ alkyl, and $R^2$ and $R^3$ are hydrogen, and $R^5$ and $R^6$ are $C_1$ to $C_{10}$ alkyl, and where $R^5$ and $R^6$ join to form a 5 membered ring structure.

25. The process of claim 1 wherein $R^4$ and $R^7$ are, independently, selected from the group consisting of methyl, ethyl, propyl, butyl, pentyl, heptyl, hexyl, octyl, nonyl, decyl and isomers thereof, and where $R^5$ and $R^6$ join to form a 5 membered ring structure.

26. The process of claim 1 wherein $R^4$ and $R^7$ are, independently, a $C_1$ to $C_{10}$ alkyl, and where $R^5$ and $R^6$ join to form a 5 membered ring structure.

27. The process of claim 1 wherein each $R^3$ is hydrogen; each $R^4$ is independently a $C_1$-$C_{10}$ alkyl; each $R^2$ is independently hydrogen; each $R^7$ is independently $C_1$-$C_{10}$ alkyl; each $R^5$ and $R^6$ is independently hydrogen, $C_1$-$C_{50}$ substituted or unsubstituted hydrocarbyl, or $C_1$-$C_{50}$ substituted or unsubstituted halocarbyl; and $R^4$ and $R^5$, $R^5$ and $R^6$ and/or $R^6$ and $R^7$ are optionally bonded together to form a ring structure; J is a bridging group represented by the formula $R^a{}_2J$, where J is C or Si, and each $R^a$ is, independently, $C_1$ to $C_{20}$ substituted or unsubstituted hydrocarbyl, and the two $R^a$ form a cyclic structure incorporating J and the cyclic structure is optionally a saturated or partially saturated cyclic or fused ring system; and each X is a univalent anionic ligand, or two Xs are joined and bound to the metal atom to form a metallocycle ring, or two Xs are joined to form a chelating ligand, a diene ligand, or an alkylidene ligand.

28. The process of claim 1 wherein the cyclic olefin monomer comprises one or more of cyclopentadiene, cyclooctadiene, norbornadiene, dicyclopentadiene, 5-ethylidene-2-norbornene, 5-methylidene-2-norbornene, vinylcyclohexene, 5-vinyl-2-norbornene, tricyclo[4.2.1.0$^{2,5}$]nona-3,7-diene, or higher ring containing diolefins with or without substituents at various ring positions.

29. The process of claim 1 wherein the cyclic olefin monomer is dicyclopentadiene, 5-ethylidene-2-norbornene, 5-methylidene-2-norbornene, or 5-vinyl-2-norbornene.

* * * * *